United States Patent
Qu et al.

(10) Patent No.: US 11,965,037 B2
(45) Date of Patent: Apr. 23, 2024

(54) ANTI-HER3 HUMANIZED MONOCLONAL ANTIBODY

(71) Applicant: SHANGHAI INSTITUTE OF BIOLOGICAL PRODUCTS CO., LTD., Shanghai (CN)

(72) Inventors: Aidong Qu, Shanghai (CN); Hongyuan Liang, Shanghai (CN); Fanhong Xu, Shanghai (CN); Aoxiang Li, Shanghai (CN); Lina Wu, Shanghai (CN); Jingye Zhu, Shanghai (CN); Jianhua Qiu, Shanghai (CN); Jin Lu, Shanghai (CN); Lin Zhang, Shanghai (CN); Xin Zhao, Shanghai (CN); Xiaofei Song, Shanghai (CN)

(73) Assignee: SHANGHAI INSTITUTE OF BIOLOGICAL PRODUCTS CO., LTD., Shanghai (CN)

( * ) Notice: Subject to any disclaimer, the term of this patent is extended or adjusted under 35 U.S.C. 154(b) by 588 days.

(21) Appl. No.: 17/260,442

(22) PCT Filed: Jul. 17, 2019

(86) PCT No.: PCT/CN2019/096418
§ 371 (c)(1),
(2) Date: Jan. 14, 2021

(87) PCT Pub. No.: WO2020/015687
PCT Pub. Date: Jan. 23, 2020

(65) Prior Publication Data
US 2021/0277144 A1 Sep. 9, 2021

(30) Foreign Application Priority Data
Jul. 17, 2018 (CN) .......................... 201810784050.1

(51) Int. Cl.
C07K 16/32 (2006.01)
A61K 47/68 (2017.01)
A61P 35/00 (2006.01)
C07K 14/71 (2006.01)
A61K 39/00 (2006.01)

(52) U.S. Cl.
CPC .......... *C07K 16/32* (2013.01); *A61K 47/6851* (2017.08); *A61P 35/00* (2018.01); *C07K 14/71* (2013.01); *A61K 2039/505* (2013.01)

(58) Field of Classification Search
CPC .... C07K 16/32; C07K 14/71; C07K 16/2863; C07K 14/7051; C07K 2317/24; C07K 2317/92; C07K 2317/94; C07K 2319/03; C07K 2317/21; C07K 2317/51; C07K 2317/515; C07K 2317/56; A61K 47/6851; A61K 2039/505; A61K 2039/507; A61K 47/68; A61P 35/00
See application file for complete search history.

(56) References Cited

FOREIGN PATENT DOCUMENTS

| CN | 103890010 A | 6/2014 | |
|----|-------------|--------|--|
| CN | 104861068 A | 8/2015 | |
| CN | 105367657 A | * 3/2016 | ............. C07K 16/28 |

OTHER PUBLICATIONS

Muhammad et al. (2017) CAR T-cells for cancer therapy, Biotechnology and Genetic Engineering Reviews, 33:2, 190-226, DOI: 10.1080/02648725.2018.1430456. pp. 191 and 194.*
Ravetch JV, Kinet JP. Fc receptors. Annu Rev Immunol. 1991;9:457-92. doi: 10.1146/annurev.iy.09.040191.002325. PMID: 1910686. p. 457.*
Schroeder HW Jr, Cavacini L. Structure and function of immunoglobulins. J Allergy Clin Immunol. Feb. 2010;125(2 Suppl 2):S41-52. doi: 10.1016/j.jaci.2009.09.046. PMID: 20176268; PMCID: PMC3670108. Entire document.*
Tiller KE, Tessier PM. Advances in Antibody Design. Annu Rev Biomed Eng. 2015;17:191-216. doi: 10.1146/annurev-bioeng-071114-040733. Epub Aug. 14, 2015. PMID: 26274600; PMCID: PMC5289076. p. 195.*
Sela-Culang I, Kunik V, Ofran Y. The structural basis of antibody-antigen recognition. Front Immunol. Oct. 8, 2013;4:302. doi: 10.3389/fimmu.2013.00302. PMID: 24115948; PMCID: PMC3792396. pp. 7-8.*
Tiller KE, Li L, Kumar S, Julian MC, Garde S, Tessier PM. Arginine mutations in antibody complementarity-determining regions display context-dependent affinity/specificity trade-offs. J Biol Chem. Oct. 6, 2017;292(40):16638-16652. doi: 10.1074/jbc.M117.783837. PMID: 28778924; PMCID: PMC5633126. p. 16638.*
Güssow D, Seemann G. Humanization of monoclonal antibodies. Methods Enzymol. 1991;203:99-121. doi: 10.1016/0076-6879(91)03007-4. PMID: 1762576. Entire document.*
Winkler K, Kramer A, Küttner G, Seifert M, Scholz C, Wessner H, Schneider-Mergener J, Höhne W. Changing the antigen binding specificity by single point mutations of an anti-p24 (HIV-1) antibody. J Immunol. Oct. 15, 2000;165(8): 4505-14. doi: 10.4049/jimmunol.165.8.4505. PMID: 11035090. p. 4505.*

(Continued)

*Primary Examiner* — Julie Wu
*Assistant Examiner* — Carol Ann Chase
(74) *Attorney, Agent, or Firm* — Michael Best & Friedrich LLP

(57) ABSTRACT

Provided is an anti-HER3 humanized monoclonal antibody. The antibody binds HER3 antigen, has high affinity and biological activity and low immunogenicity, and is stable in structure. The antibody can be used for preparing drugs for preventing or treating HER3-related diseases.

15 Claims, 3 Drawing Sheets
Specification includes a Sequence Listing.

(56) References Cited

OTHER PUBLICATIONS

Translation of International Search Report and Written Opinion for Application No. PCT/CN2019/096418 dated Oct. 15, 2019 (8 pages).
Jones et al., "Replacing the complementarity-determining regions in a human antibody with those from a mouse", Nature, vol. 321, 1986, pp. 522-525.
Queen et al., "A humanized antibody that binds to the interleukin 2 receptor", Proc. Natl. Acad. Sci., vol. 86, 1989, pp. 10029-10033.
Carter et al., "Humanization of an anti-p185HER2 antibody for human cancer therapy", Proc. Natl. Acad. Sci., vol. 89, 1992, pp. 4285-4289.
Pedersen et al., "Comparison of Surface Accessible Residues in Human and Murine Immunoglobulin Fv Domains", 1994, J. Mol. Biol., vol. 235, 1994, pp. 959-973.
Hsiao et al., "Humanization of 60.3, an anti-CD18 antibody; importance of the L2 loop", Protein Engineering, vol. 7, No. 6, 1994, pp. 815-822.
Jespers et al., "Guiding the Selection of Human Antibodies from Phage Display Repertoires to a Single Epitope of an Anitgen", Bio/Technology, vol. 12, 1994, pp. 899-903.

\* cited by examiner a. Light chain variable region

```
              10          20          30          40          50
m_VL    DIVMTQAAFS  NPVTLGTSAS  ISCRSSKSLL  HSNGITYLYW  YLQKPGQSPQ
h_VL    EIVLTQSPGT  LSLSPGERAT  LSCRSSKSLL  HSNGITYLYW  YQQKPGQAPR 60          70          80          90         100
m_VL    LLIYQMSNL   ASGVPDRFSGS  GSGTDFTLRI  SRVEAEDVGV  YYCAQNLELP
h_VL    LLIYQMSNL   ASGIPDRFSGS  GSGTDFTLTI  SRLEPEDFAV  YYCAQNLELP 110
m_VL    WTFGQGTKLE  IK    (SEQ ID No.: 5)
h_VL    WTFGQGTKVE  IK    (SEQ ID No.: 9)
``` b. Heavy chain variable region

```
              10          20          30          40          50
m_VH    EVQLQQSGTE  LMKPGASVKI  SCKATGGTFS  NYWIDWVKQR  PGQGLEWIGE
h_VH    QVQLVQSGAE  VKKPGSSVKV  SCKASGGTFS  NYWIDWVRQA  PGQGLEWIGE 60          70          80          90         100
m_VH    ILPGSGGTDY  NEKFKGKATF  TADTSSNTAY  MQLSSLTSED  SAVYYCARDD
h_VH    ILPGSGGTDY  NEKFKGRVTI  TADESTSTAY  MELSSLRSED  TAVYYCARDD 110
m_VH    YDVFAYWGQG  TLVTVSA    (SEQ ID No.: 6)
h_VH    YDVFAYWGQG  TLVTVSS    (SEQ ID No.: 10)
```

Figure 1

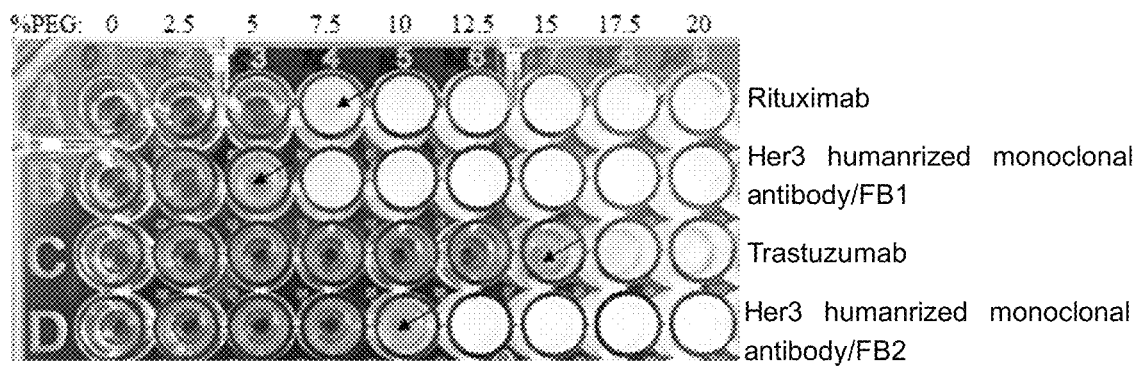

Figure 2

ANTI-HER3 HUMANIZED MONOCLONAL ANTIBODY

CROSS-REFERENCE TO RELATED APPLICATION(S)

This application is a U.S. national stage filing under 35 U.S.C. § 371 of International Patent Application No. PCT/CN2019/096418, filed on Jul. 17, 2019, which claims priority to and the benefit of Chinese Patent Application No. 201810784050.1, filed on Jul. 17, 2018, the entire contents of each of which are fully incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 11,079 bytes ASCII (Text) file named "P2020-2615-1PCUS-208330-9012-US01-SEQ-LIST-02-18-21.txt" created on Feb. 18, 2021.

TECHNICAL FIELD

The present invention relates to the field of medicine, in particular to the anti-HER3 humanized monoclonal antibody and the preparation thereof.

BACKGROUND

More and more studies have found that human epidermal growth factor receptor 3 (HER3) plays an important role in tumor occurrence and progression. HER3 usually functions by forming a heterodimer with EGFR or HER2 molecules. In cancer pathological tissues, EGFR and HER2 overexpressions are often accompanied by overexpression of HER3, and it is believed that HER3 overexpression is significant for drug resistance in EGFR, HER2 targeted therapy. The conformation of HER3 is changed after binding with the ligand Heregulin (HRG), exposing the binding sites to EGFR and HER2, and then forming heterodimers with EGFR and HER2 molecules, to activate intracellular signals and promote tumor cell proliferation.

Because mouse monoclonal antibody can cause human anti-mouse antibody (HAMA) response during clinical treatment, it is limited in clinical treatment. Antibody humanization technology can greatly reduce the immunogenicity of mouse monoclonal antibodies.

Therefore, in view of the role and function of HER3 in various related diseases, it still needs to develop anti-HER3 humanized antibodies suitable for treating patients in this field.

SUMMARY OF THE INVENTION

The purpose of the present invention is to provide an HER3 humanized antibody with high affinity and high biological activity and the application thereof.

In a first aspect of the present invention, it provides a light chain variable region of an antibody, wherein the light chain variable region is selected from the group consisting of:
  (1) a light chain variable region with a sequence shown in SEQ ID NO: 1; or
  (2) a derivative light chain variable region derived from the sequence shown in SEQ ID NO: 1, having the function of the light chain variable region described in (1), which is obtained by substitution, deletion, modification and/or addition of at least one (such as 1-20, preferably 1-15, more preferably 1-10, more preferably 1-8, more preferably 1-3, most preferably 1 or 2) amino acid residue of the amino acid sequence shown in SEQ ID NO: 1.

In another preferred embodiment, the substitution, deletion, modification and/or addition of amino acid residues does not occur in CDR region, but in framework region.

In another preferred embodiment, a glycine (G) in the light chain variable region is mutated, which is at the position corresponding to position 69 in the sequence shown in SEQ ID NO: 1.

In another preferred embodiment, a glycine (G) in the light chain variable region is mutated into serine (S) (i.e., G69S), which is at the position corresponding to position 69 in the sequence shown in SEQ ID NO: 1.

In another preferred embodiment, an isoleucine (I) in the light chain variable region is mutated, which is at the position corresponding to position 63 in the sequence shown in SEQ ID NO: 1.

In another preferred embodiment, an Ile in the light chain variable region is mutated into Val (i.e., Ile→Val), which is at the position corresponding to position 63 in the sequence shown in SEQ ID NO: 1.

In another preferred embodiment, the light chain variable region has a sequence shown in SEQ ID NO: 1 or 3 or 7.

In a second aspect of the present invention, it provides a light chain of an antibody, wherein the light chain comprises the light chain variable region according to the first aspect of the present invention.

In another preferred embodiment, the light chain of the antibody further comprises a heavy chain constant region.

In another preferred embodiment, the light chain constant region is of human, mouse or rabbit, preferably of human.

In a third aspect of the present invention, it provides a heavy chain variable region of an antibody, wherein the heavy chain variable region is selected from the group consisting of:
  (i) a heavy chain variable region with a sequence shown in SEQ ID NO: 2; or
  (ii) a derivative heavy chain variable region derived from the sequence shown in SEQ ID NO: 2, having the function of the heavy chain variable region described in (i), which is obtained by substitution, deletion, modification and/or addition of at least one (such as 1-20, preferably 1-15, more preferably 1-10, more preferably 1-8, more preferably 1-3, most preferably 1 or 2) amino acid residue of the amino acid sequence shown in SEQ ID NO: 2.

In another preferred embodiment, the substitution, deletion, modification and/or addition of amino acid residues does not occur in CDR regions, but in framework regions.

In another preferred embodiment, the heavy chain variable region has the amino acid mutation at a position corresponding to the position in sequence shown in SEQ ID NO: 2 selected from the group consisting of: arginine (R) at position 38, methionine (M) at position 48, arginine (R) at position 67, valine (V) at position 68, and a combination thereof.

In another preferred embodiment, the mutation of the heavy chain variable region is selected from the following group: R38K, M48I, V68A, R67K, and a combination thereof, wherein the positions correspond to the sequence shown in SEQ ID NO: 2;

preferably, the mutation is R38K, or R67K+V68A.

In another preferred embodiment, an arginine (R) in the heavy chain variable region is mutated, which is at the position corresponding to position 67 in the sequence shown in SEQ ID NO: 2.

In another preferred embodiment, the heavy chain variable region has a mutation selected from the group consisting of: R67K, wherein the position corresponds to the position in the sequence shown in SEQ ID NO: 2.

In another preferred embodiment, the heavy chain variable region has a sequence shown in SEQ ID NO: 2 or 4 or 8.

In another preferred embodiment, the heavy chain variable region has a sequence shown in SEQ ID NO: 2, and has a mutation selected from the group consisting of:

Arg→Lys (R38K) at position 38 in VH, Met→Ile (M48I) at position 48 in VH, Val→Ala (V68A) at position 68 in VH, Arg→Lys (R67K) at position 67 in VH, and Val→Ala (V68A) at position 68 in VH.

In a fourth aspect of the present invention, it provides a heavy chain of an antibody, wherein the heavy chain comprises the heavy chain variable region according to the third aspect of the present invention.

In another preferred embodiment, the heavy chain of the antibody further comprises a heavy chain constant region.

In another preferred embodiment, the heavy chain constant region is of human, mouse or rabbit, preferably of human.

In a fifth aspect of the present invention, it provides an antibody, wherein the antibody comprises:
 (1) the light chain variable region according to the first aspect of the present invention; and/or
 (2) the heavy chain variable region according to the third aspect of the present invention;
 alternatively, the antibody comprises: the light chain according to the second aspect of the present invention; and/or the heavy chain according to the fourth aspect of the present invention, In another preferred embodiment, the antibody has a light chain variable region as shown in SEQ ID NO: 1 or 3; and/or a heavy chain variable region as shown in SEQ ID NO: 2 or 4.

In another preferred embodiment, the antibody has a mutation selected from the group consisting of:
 (a) a glycine (G) in the light chain variable region of the antibody is mutated, which is at the position corresponding to position 69 in the sequence shown in SEQ ID NO: 1; and/or
 (b) the heavy chain variable region of the antibody has the amino acid mutation at a position corresponding to the position in sequence shown in SEQ ID NO: 2 selected from the group consisting of: Arginine (R) at position 38, methionine (M) at position 48, valine (V) at position 68, and a combination thereof.

In another preferred embodiment, a glycine (G) in the light chain variable region of the antibody is mutated, which is at the position corresponding to position 69 in the sequence shown in SEQ ID NO: 1.

In another preferred embodiment, the antibody has the amino acid mutation at a position corresponding to the position in the heavy chain variable region sequence shown in SEQ ID NO: 2 selected from the group consisting of: arginine (R) at position 38, methionine (M) at position 48, valine (V) at position 68, and a combination thereof.

In another preferred embodiment, a glycine (G) in the light chain variable region of the antibody is mutated into serine (S), which is at the position corresponding to position 69 in SEQ ID NO: 1, and an arginine (R) in the heavy chain variable region of the antibody is mutated into lysine (K), which is at the position corresponding to the position 38 in the sequence shown in SEQ ID NO: 2.

In another preferred embodiment, the sequence of the light chain variable region of the antibody is shown in SEQ ID NO: 1 or 3; and/or the sequence of the heavy chain variable region of the antibody is shown in SEQ ID NO: 2 or 4.

In another preferred embodiment, the sequence of the light chain variable region of the antibody is shown in SEQ ID NO: 3; and the sequence of the heavy chain variable region of the antibody is shown in SEQ ID NO: 2 or 4.

In another preferred embodiment, the antibody has a light chain variable region with a sequence shown in SEQ ID NO: 3; and the antibody has a heavy chain variable region with a sequence shown in SEQ ID NO: 4.

In another preferred embodiment, the antibody is a humanized antibody.

In another preferred embodiment, the antibody specifically binds to HER3.

In another preferred embodiment, the KD value (M) of the affinity of the antibody to human HER3 is from 1.0E-8 to 2.0E-10.

In another preferred embodiment, the antibody is a double-chain antibody or a single-chain antibody.

In another preferred embodiment, the antibody is a monoclonal antibody.

In another preferred embodiment, the antibody is a bispecific antibody.

In another preferred embodiment, the antibody is in the form of a drug conjugate.

In a sixth aspect of the present invention, it provides a recombinant protein, wherein the recombinant protein comprises:
 (i) the light chain variable region according to the first aspect of the present invention, the light chain according to the second aspect of the present invention, the heavy chain variable region according to the third aspect of the present invention, and the heavy chain according to the fourth aspect of the present invention, or the antibody according to the fifth aspect of the present invention; and
 (ii) an optional tag sequence to assist expression and/or purification.

In another preferred embodiment, the tag sequence comprises a 6His tag.

In another preferred embodiment, the recombinant protein (or polypeptide) comprises a fusion protein.

In another preferred embodiment, the recombinant protein is a monomer, dimer, or multimer.

In a seventh aspect of the present invention, it provides an antibody preparation, wherein the antibody preparation comprises:
 (a) the antibody according to the fifth aspect of the present invention, and
 (b) a carrier, which includes buffers, sterile water, and optional surfactants.

In another preferred embodiment, the concentration of the antibody in the preparation is 5-100 mg/mL; preferably 10-70 mg/mL; more preferably 20-60 mg/mL.

In another preferred embodiment, the buffer is selected from the group consisting of: a citric acid buffer system, a histidine buffer system, and a combination thereof.

In another preferred embodiment, the buffer is a histidine buffer system.

In another preferred embodiment, the concentration of the histidine buffer system in the preparation is 0.5-20 mM, preferably 1-10 mM.

In another preferred embodiment, the citric acid buffer system contains histidine and histidine hydrochloride, and preferably contains 1-10 mM of histidine and 1-10 mM of histidine hydrochloride, in the total weight of the antibody preparation.

In another preferred embodiment, the buffer is a citric acid buffer system.

In another preferred embodiment, the concentration of the citric acid buffer system in the preparation is 5-100 mM, preferably 10-50 mM.

In another preferred embodiment, the citric acid buffer system contains sodium citrate and sodium chloride, and preferably contains 10-50 mM of sodium citrate and 50-200 mM of sodium chloride, in the total weight of the antibody preparation.

In another preferred embodiment, the surfactant is selected from the group consisting of: Tween 80, Tween 20, and a combination thereof.

In another preferred embodiment, the content of the surfactant in the preparation is 0.005-0.2 wt %, in the total weight of the antibody preparation.

In another preferred embodiment, the surfactant is Tween 80 with a concentration of 0.02-0.1 wt %.

In another preferred embodiment, the pH of the preparation ranges from 5.0 to 7.5, preferably from 5.5 of 7.

In another preferred embodiment, the preparation is an injection preparation.

In another preferred embodiment, the preparation comprises: the antibody of the fifth aspect of the present invention, a histidine buffer system, a surfactant, and a supplemental volume of sterile water for injection.

In another preferred embodiment, the preparation comprises:
the antibody of the fifth aspect of the present invention 20-60 mg/mL;
histidine buffer system 1-10 mM;
Tween 80 0.02-0.1 wt %;
and a supplemental volume of sterile water for injection, and the pH of the preparation is preferably in the range of 5.5-6.5.

In an eighth aspect of the present invention, it provides a kit, wherein the kit comprises the antibody preparation according to the seventh aspect of the present invention, and a container for containing the antibody preparation.

In a ninth aspect of the present invention, it provides a CAR construct, wherein the scFv segment of the antigen binding domain of the CAR construct is the binding region specifically binding to HER3, and the ScFv has the light chain variable region according to the first aspect of the present invention and the heavy chain variable region according to the third aspect of the present invention.

In a tenth aspect of the present invention, it provides a recombinant immune cell, wherein the immune cell expresses an exogenous CAR construct according to the ninth aspect of the present invention.

In another preferred embodiment, the immune cell is selected from the group consisting of: NK cells and T cells.

In another preferred embodiment, the immune cell is derived from human or a non-human mammal (such as a mouse).

In an eleventh aspect of the present invention, it provides an antibody-drug conjugate, wherein the antibody-drug conjugate comprises:

(a) an antibody moiety, wherein the antibody moiety is selected from the group consisting of: the heavy chain variable region according to the first aspect of the present invention, the heavy chain according to the second aspect of the present invention, the light chain variable region according to the third aspect of the present invention, the light chain according to the fourth aspect of the present invention, and the antibody according to the fifth aspect of the present invention, and a combination thereof; and (b) a coupling moiety coupled to the antibody moiety, which is selected from the group consisting of a detectable label, a drug, a toxin, a cytokine, a radionuclide, an enzyme, and a combination thereof.

In another preferred embodiment, the antibody moiety and the coupling moiety are coupled through a chemical bond or a linker.

In a twelfth aspect of the present invention, it provides a use of an active ingredient selected from the group consisting of: the heavy chain variable region according to the first aspect of the present invention, the heavy chain according to the second aspect of the present invention, the light chain variable region according to the third aspect of the present invention, the light chain according to the fourth aspect of the present invention, the antibody according to the fifth aspect of the present invention, the recombinant protein according to the sixth aspect of the present invention, the immune cell according to the tenth aspect of the present invention, the antibody-drug conjugate according to the eleventh aspect of the present invention, and combinations thereof, wherein the active ingredient is used for (a) preparation of detection reagents or kits;
(b) preparation of drugs or preparations for preventing and/or treating HER3 related diseases; and/or
(c) preparation of drugs or preparations for preventing and/or treating cancer or tumors.

In another preferred embodiment, the tumor is selected from the group consisting of: hematological tumors, solid tumors, and a combination thereof.

In another preferred embodiment, the hematological tumor is selected from the group consisting of: acute myeloid leukemia (AML), multiple myeloma (MM), chronic lymphocytic leukemia (CLL), acute lymphocytic leukemia (ALL), diffuse large B cell lymphoma (DLBCL), Hodgkin's lymphoma, and a combination thereof.

In another preferred embodiment, the solid tumor is selected from the group consisting of: gastric cancer, gastric cancer peritoneal metastasis, liver cancer, leukemia, kidney tumor, lung cancer, small intestine cancer, bone cancer, prostate cancer, colorectal cancer, breast cancer, colorectal cancer, cervical cancer, ovarian cancer, lymphoma, nasopharyngeal cancer, adrenal gland tumor, bladder tumor, non-small cell lung cancer (NSCLC), brain glioma, endometrial cancer, and a combination thereof.

In another preferred embodiment, the tumor is a tumor that highly expresses HER3.

In another preferred embodiment, the drug or preparation is used for preparation of a drug or preparation for preventing and/or treating HER3 (positive expression) related diseases.

In another preferred embodiment, the antibody is in the form of a drug conjugate (ADC).

In another preferred embodiment, the detection reagent or kit is used for diagnosis of HER3 related diseases.

In another preferred embodiment, the detection reagent or kit is used for detection of HER3 protein in a sample.

In another preferred embodiment, the detection reagent is a detection piece.

In a thirteenth aspect of the present invention, it provides a pharmaceutical composition, wherein the pharmaceutical composition comprises:

(i) an active ingredient, wherein the active ingredient is selected from the group consisting of: the heavy chain variable region according to the first aspect of the present invention, the heavy chain according to the second aspect of the present invention, the light chain variable region according to the third aspect of the present invention, the light chain according to the fourth aspect of the present invention, the antibody according to the fifth aspect of the present invention, the recombinant protein according to the sixth aspect of the present invention, the immune cell according to the tenth aspect of the present invention, the antibody-drug conjugate according to the eleventh aspect of the present invention, and a combination thereof; and (ii) a pharmaceutically acceptable carrier.

In another preferred embodiment, the pharmaceutical composition is a liquid preparation.

In another preferred embodiment, the pharmaceutical composition is an injection.

In another preferred embodiment, the pharmaceutical composition is used for treating tumors.

In another preferred embodiment, the tumor is a tumor that highly expresses HER3.

In a fourteenth aspect of the present invention, it provides a polynucleotide, which encodes a polypeptide selected from the group consisting of:

(1) the heavy chain variable region according to the first aspect of the present invention, the heavy chain according to the second aspect of the present invention, the light chain variable region according to the third aspect of the present invention, the light chain according to the fourth aspect of the present invention, or the antibody according to the fifth aspect of the present invention; or (2) the recombinant protein according to the sixth aspect of the present invention;

(3) the CAR construct according to the ninth aspect of the present invention.

In a fifteenth aspect of the present invention, it provides a vector, which contains the polynucleotide according to the fourteenth aspect of the present invention.

In another preferred embodiment, the vector includes: bacterial plasmid, phage, yeast plasmid, plant cell virus, mammalian cell virus such as adenovirus, retrovirus, or other vectors.

In a sixteenth aspect of the present invention, it provides a genetically engineered host cell, wherein the host cell contains the vector according to the fifteenth aspect of the present invention or the genome thereof is integrated with the polynucleotide according to the fourteenth aspect of the present invention.

In a seventeenth aspect of the present invention, it provides a method for in vitro detection (including diagnostic or non-diagnostic) of HER3 protein in a sample, wherein the method comprises the steps:

(1) in vitro contacting the sample with the antibody according to the fifth aspect of the present invention;

(2) detecting whether an antigen-antibody complex is formed, wherein the formation of the complex indicates the presence of HER3 protein in the sample.

In an eighteenth aspect of the present invention, it provides a detection plate, wherein the detection plate comprises: a substrate (support plate) and a detection strip, wherein the detection strip comprises the antibody according to the fifth aspect of the present invention, or the antibody conjugate according to the eleventh aspect of the present invention.

In a nineteenth aspect of the present invention, it provides a kit, which comprises:

(1) a first container, which contains the antibody according to the fifth aspect of the present invention; and/or (2) a second container, which contains a secondary antibody against the antibody according to the fifth aspect of the present invention;

alternatively, the kit comprises the detection plate according to the eighteenth aspect of the present invention.

In a twentieth aspect of the present invention, it provides a method for preparing a recombinant polypeptide, wherein the method comprises:

(a) culturing the host cell according to the fourteenth aspect of the present invention under conditions suitable for expression;

(b) isolating a recombinant polypeptide from the culture, wherein the recombinant polypeptide is the antibody according to the fifth aspect of the present invention or the recombinant protein according to the sixth aspect of the present invention.

In a twenty-first aspect of the present invention, it provides a method for treating HER3 related diseases, wherein the method comprises: administering the antibody according to the fifth aspect of the present invention, an antibody-drug conjugate of the antibody, or a CAR-T cell expressing the antibody, or a combination thereof to a subject in need.

It should be understood that within the scope of the present invention, the various technical features of the present invention above and the various technical features specifically described hereinafter (as in the embodiments) may be combined with each other to constitute a new or preferred technical solution. Due to space limitations, it is not repeated here.

DESCRIPTION OF THE FIGURES

FIG. 1 shows the sequences of the variable regions of the HER3 mouse monoclonal antibody and the human Germline template. Wherein, a is the light chain variable region, and b is the heavy chain variable region. The upper rows are the mouse monoclonal antibody variable region sequences (SEQ ID NO: 5 or 6), and the lower rows are the variable region sequences after CDR transplantation (SEQ ID NO: 9 or 10). The underlined parts are the CDR regions, and amino acids of the gray marked parts are the different amino acids in the framework region between the mouse monoclonal antibody and the human Germline template.

FIG. 2 shows the solubility results of PEG precipitation method, and the arrows show the wells where precipitation begins.

DETAILED DESCRIPTION

Figure 3:
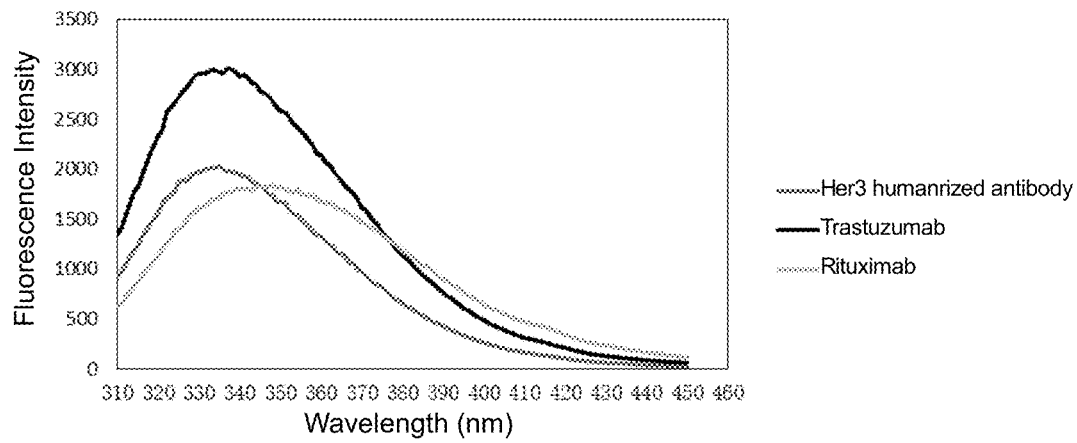
FIG. 3 shows the endogenous fluorescence detection plot of the humanized antibody of the present invention.

By extensively and intensively studies, through largely screening, the inventors unexpectedly obtained an anti- HER3 humanized antibody with excellent affinity and good structural stability. Specifically, when selecting a humanized framework region in the present invention, both similarity and frequency of use in the human body were taken into consideration, and the framework regions of two sequences of IGKV3-20*01 and IGHV1-69*01 were selected for humanization, and mutation screen was conducted on the obtained humanized antibody. The humanized antibody, especially the mutant humanized antibody, can achieve an affinity similar to that of the chimeric antibody. Through preliminary studies on the solubility and endogenous fluorescence of the humanized antibody, it was confirmed that the humanized antibody has preliminary druggability, and is promising to be further developed into humanized monoclonal antibody drugs for targeted therapy in the future. A preliminary druggability study was conducted on the humanized antibody, and the formulation of the anti-HER3 humanized antibody was screened and determined. On this basis, the present invention has been completed.

The Terms

To make it easier to understand the present invention, certain technical and scientific terms are specifically defined below. Unless otherwise clearly defined herein, all other technical and scientific terms used herein have meanings commonly understood by those skilled in the art in the field to which the present invention belongs.

The three-letter codes and one-letter codes of amino acids used in the present invention are as described in J. biol. chem, 243, p 3558 (1968).

As used herein, the terms "administration" and "treatment" refer to the application of exogenous drugs, therapeutic agents, diagnostic agents or compositions to animals, humans, subjects, cells, tissues, organs or biological fluids. "Administration" and "treatment" can refer to treatment, pharmacokinetics, diagnosis, research and experimental methods. The treatment of cells includes contacting the reagents with cells, contacting the reagents with fluids, and contacting the fluids with cells. "Administration" and "treatment" also refer to treatment by reagents, diagnostics, binding compositions, or by another cells in vitro and ex vivo. When "treatment" is applied to humans, animals or research subjects, it refers to treatment, prevention or preventive measures, research and diagnosis, including contacting the anti-HER3 antibodies with humans or animals, subjects, cells, tissues, physiological compartments or physiological fluids.

As used herein, the term "treatment" refers to the administration of an internal or external therapeutic agent, including any one of the anti-HER3 antibodies and compositions of the present invention, to a patient who has one or more disease symptoms, wherein the therapeutic agent is known to have a therapeutic effect on these symptoms. Usually, the therapeutic agent is administered to a patient with an amount effective to alleviate one or more disease symptoms (a therapeutically effective amount).

As used herein, the term "optional" or "optionally" means that the event or situation described thereafter may occur, but not necessarily. For example, "optionally comprises 1-3 antibody heavy chain variable regions" means that the antibody heavy chain variable region of a specific sequence may be comprised but does not have to be comprised, and number can be 1, 2 or 3.

The "sequence identity" in the present invention means the degree of identity between two nucleic acid or two amino acid sequences when optimally aligned and compared, with appropriate mutations such as substitutions, insertions or deletions. The sequence identities between the sequences and their identical sequences described in the present invention may be at least 85%, 90% or 95%, preferably at least 95%. Non-limiting examples include 85%, 86%, 87%, 88%, 89%, 90%, 91%, 92%, 93%, 94%, 95%, 96%, 97%, 98%, 99%, 100%.

HER3

Human epidermal growth factor receptor 3 (HER3) plays an important role in tumor occurrence and progression. HER3 usually functions by forming a heterodimer with EGFR or HER2 molecules. In cancer pathological tissues, EGFR and HER2 overexpressions are often accompanied by overexpression of HER3, and it is believed that HER3 overexpression is significant for drug resistance in EGFR, HER2 targeted therapy. The conformation of HER3 is changed after binding with the ligand Heregulin (HRG), exposing the binding sites to EGFR and HER2, and then forming heterodimers with EGFR and HER2 molecules, to activate intracellular signals and promote tumor cell proliferation.

Anti-HER3 mouse monoclonal antibody 1044 (Application No. 2014104015453) blocks the binding of HER3 molecule to its ligand HRG, thereby inhibiting the formation of heterodimerizations with other molecules of the HER family. This antibody can bind to the HER3 molecule on the tumor surface and inhibit the proliferation of human epidermal squamous cell carcinoma A431 cells, and has the potential to treat a variety of HER3 overexpressing tumors.

1044 mouse monoclonal antibody light chain variable region (SEQ ID NO: 5)
DIVMTQAAFSNPVTLGTSASISC<u>RSSKSLLHSNGI-TYLY</u>WYLQKPGQSPQLLI<u>YQMSN-LASG</u>VPDRFSSSGSGTDFTLRISRVEAEDVGVYY-CA<u>QNLELPWT</u>FGGGT KLEIKR 1044 mouse monoclonal antibody heavy chain variable region (SEQ ID NO: 6)
EVQLQQSGTELMKPGASVKISCKAT<u>GGTFSNY-WID</u>WVKQRPGHGLEWIG<u>EI LPGSGGT-DYNEKFKG</u>KATFTADTSSNTAYMQLSSLTSED-SAVYYCAR<u>DDYDVFA</u>YWGQGTLVTVSA Antibody As used herein, the term "antibody" refers to an immunoglobulin, which is a tetrapeptide chain structure composed of two identical heavy chains and two identical light chains connected by interchain disulfide bonds. The amino acid composition and sequence of the constant region of the immunoglobulin heavy chain varies, so the antigenicity varies. Accordingly, immunoglobulins can be divided into five classes, or isotypes of immunoglobulins, namely IgM, IgD, IgG, IgA and IgE, and their corresponding heavy chains are µ chain, δ chain, γ chain, α chain, and ε chain, respectively. Ig of the same class can be divided into different subclasses according to the difference in the amino acid compositions of the hinge regions and the numbers and positions of heavy chain disulfide bonds. For example, IgG can be divided into IgG1, IgG2, IgG3, IgG4. Light chains are divided into κ chain and λ chain according to the difference of the constant regions. Each of the five types of Ig can comprise a κ chain or a λ chain. The subunit structures and three-dimensional configurations of different classes of immunoglobulins are well known to those skilled in the art.

The antibody light chain of the present invention may further comprise a light chain constant region, which comprises a human or mouse κ, λ chain or a variant thereof.

In the present invention, the antibody heavy chain of the present invention may further comprise a heavy chain constant region, which comprises a human or mouse IgG1, IgG2, IgG3, IgG4 or a variant thereof. The sequence of about 110 amino acids near the N terminal of the antibody heavy chain or light chain varies greatly and is a variable region (Fv region); while the remaining amino acid sequence close to the C terminal is relatively stable and is a constant region. Variable regions comprise 3 hypervariable regions (HVR) and 4 framework regions (FR) with relatively conserved sequences. The 3 hypervariable regions determine the specificity of the antibody, also known as the complementary determining regions (CDRs). Each light chain variable region (LCVR) and heavy chain variable region (HCVR) consist of 3 CDR regions and 4 FR regions, with an order from the amino terminal to the carboxyl terminal of: FR1, CDR1, FR2, CDR2, FR3, CDR3 and FR4. The 3 CDR regions of the light chain refer to LCDR1, LCDR2 and LCDR3; the 3 CDR regions of the heavy chain refer to HCDR1, HCDR2 and HCDR3.

The term "mouse antibody" in the present invention is an anti-HER3 monoclonal antibody prepared according to the knowledge and skills in the art. During preparation, the test subject was injected with the HER3 antigen, and then hybridomas expressing antibodies with the desired sequences or functional properties was isolated. In a preferred embodiment of the present invention, the mouse HER3 antibody or antigen-binding fragment thereof may further comprise a light chain constant region of a mouse κ, λ chain or a variant thereof, or further comprise a heavy chain constant region of mouse IgG1, IgG2, IgG3 or a variant thereof.

The term "chimeric antibody" is an antibody formed by fusing the variable region of a mouse antibody with the constant region of a human antibody, which can reduce the immune response induced by the mouse antibody.

The term "humanized antibody", also known as CDR-grafted antibody, refers to the antibodies produced by transplantation of mouse CDR sequences into the framework regions of human antibody variable regions (i.e., a different type of human germline antibody framework sequence). Humanized antibodies can overcome the heterogeneous reaction induced by chimeric antibodies that carry a large amount of mouse protein components. Such framework sequences can be obtained from public DNA databases or published references that include germline antibody gene sequences. In order to avoid the decrease in activity resulting from the decrease of immunogenicity, the human antibody variable region framework sequence can be subjected to minimal reverse mutations or back mutations to maintain activity.

The term "antigen-binding fragment of an antibody" (or "antibody fragment" for short) refers to one or more fragments of an antibody that retain the ability to specifically bind to an antigen (for example, HER3). It has been shown that fragments of full-length antibodies can be used to perform the antigen-binding function of antibodies. Examples of the binding fragment included in the term "antigen-binding fragment of an antibody" include:
  (i) an Fab fragment, which is a monovalent fragment consisting of VL, VH, CL and CH1 domains;
  (ii) an F(ab')$_2$ fragment, which is a bivalent fragment comprising two Fab fragments connected by a disulfide bridge on the hinge region;
  (iii) an Fd fragment consisting of VH and CH1 domains;
  (iv) an Fv fragment consisting of the VH and VL domains of one arm of an antibody.

An Fv antibody comprises a heavy chain variable region and a light chain variable region, but does not comprise a constant region, and is the smallest antibody fragment with all antigen binding sites. Generally, an Fv antibody also comprises a polypeptide linker between the VH and VL domain, and can form the structure required for antigen binding.

The term "CDR" refers to one of the 6 hypervariable regions within the variable domain of an antibody that mainly contributes to antigen binding. One of the most commonly used definitions of the 6 CDRs is provided by Kabat E. A et al., (1991) Sequences of proteins of immunological interest. NIH Publication 91-3242.

The term "epitope" or "antigenic determinant" refers to the site on an antigen where the immunoglobulin or the antibody specifically binds (for example, a specific site on the HER3 molecule). Epitope usually comprises at least 3, 4, 5, 6, 7, 8, 9, 10, 11, 12, 13, 14 or 15 consecutive or non-consecutive amino acids in a unique spatial conformation.

The terms "specific binding", "selective binding", "selectively bind", and "specifically bind", refer to the binding of an antibody to an epitope on a predetermined antigen. Usually, an antibody has an affinity (KD) that is approximately less than $10^{-7}$M, such as approximately less than $10^{-8}$M, $10^{-9}$M or $10^{-10}$ M or less.

The term "competitive binding" means that the binding of an antibody to the same epitope (also called an antigenic determinant) on the extracellular region of HER3 or a part of the same epitope, which is recognized by the monoclonal antibody of the present invention. An antibody that binds to the same epitope as the monoclonal antibody of the present invention refers to an antibody that recognizes and binds to the amino acid sequence of HER3 recognized by the monoclonal antibody of the present invention.

The term "KD" or "Kd" refers to the dissociation equilibrium constant of a specific antibody-antigen interaction. Generally, the antibody of the present invention binds to HER3 with a dissociation equilibrium constant (KD) less than about $10^{-7}$M, such as less than about $10^{-8}$M, $10^{-9}$M or $10^{-10}$M or less.

As used herein, the term "antigen determinant" refers to a discrete three-dimensional site on an antigen that is recognized by the antibody or antigen-binding fragment of the present invention.

The present invention includes not only intact antibodies, but also immunologically active fragments of antibody fragments or fusion proteins formed by antibodies and other sequences. Therefore, the present invention also includes fragments, derivatives and analogs of the antibodies.

In the present invention, antibodies include murine, chimeric, humanized, or fully human antibodies prepared by techniques well known to those skilled in the art. Recombinant antibodies, such as chimeric and humanized monoclonal antibodies, including human and non-human parts, can be prepared using DNA recombinant techniques well known in the art.

As used herein, the term "monoclonal antibody" refers to an antibody secreted by a clone derived from a single cell. Monoclonal antibodies are highly specific and direct against a single epitope. The cells may be eukaryotic, prokaryotic or phage cloned cell lines.

In the present invention, the antibody may be monospecific, bispecific, trispecific, or more multispecific.

In the present invention, the antibody of the present invention also includes conservative variants thereof, which means that compared with the amino acid sequence of the antibody of the present invention, there are at most 10, preferably at most 8, more preferably at most 5, most preferably at most 3 amino acids replaced by amino acids with the same or similar properties to form a polypeptide. These conservatively variant polypeptides are preferably produced by amino acid substitution according to Table A.

TABLE A

| Initial residue | Representative substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

Anti-HER3 Humanized Antibody

The present invention provides an anti-HER3 humanized antibody (HER3 antibody for short below). In particular, the present invention provides a humarized antibody with high specificity and high affinity against HER3, which comprises a heavy chain and a light chain, wherein the heavy chain contains a heavy chain variable region (VH) amino acid sequence, and the light chain contains a light chain variable region (VL) amino acid sequence.

In 1986, Jones et al. transplanted the mouse monoclonal antibody heavy chain CDRs into the human antibody heavy chain framework for the first time, and then assembled it with the mouse monoclonal antibody light chain to obtain a complete antibody, which maintained similar affinity to the original mouse monoclonal antibody. It provides ideas for the development of antibody humanization technology. In 1989, Queen et al. successfully constructed anti-CD25 humanized antibodies through the method of CDR transplantation. The method used human antibody Eu framework region for humanization, and the amino acids of the mouse antibody were retained in some parts of the framework region, to maintain the affinity. In 1992, Presta et al. reported a method of successfully constructing humanization by CDR transplantation using the consensus sequence of human antibody subgroups as a template. In 1994, Pedersen et al. reported the humanrization of antibodies by the method of resurfacing. In 1994, Hsiao et al. reported a humanization method of CDR transplantation with human antibody germline sequence framework region. In 1994, Jespers et al. successfully constructed a humanrization method using the shuffling library method.

There are usually two choices of human framework regions in antibody humanization. One is a known mature antibody, and the other is a human Germline sequence. Known mature antibody framework regions usually contain somatic mutation sites, which may bring potential immunogenicity. Compared with mature antibodies, the human Germline sequence framework region is theoretically less immunogenic, and has a more flexible structure, with strong plasticity, and is easy to accept different CDR regions. The frequency of use of human antibody Germline gene in the human body has a certain bias. The use of humanized antibody of the Germline framework region with high frequency has the advantages of low immunogenicity, high expression, and stable structure. Therefore, the present invention the Germline sequence with the highest similarity to the mouse antibody was not selected for humanrization. Insteadly, both the similarity and frequency of human use were taken into consideration. After a large number of experimental screenings, two frameworks of IGKV3-20*01 and IGHV1-69*01 were selected for humanrization. In the present invention, human antibody Germline framework region was selected for CDR transplantation, so that the constructed humanized antibody has a more stable structure, high expression, low immunogenicity and higher druggability.

Specifically, it was as described in the first to fifth aspects of the present invention.

1044 light chain variable region after CDR transplantation (mouse monoclonal antibody amino acids retained at sites VL1 and VL4) (SEQ ID NO: 1)
DIVMTQSPGTLSLSPGERATLSCRSSKSLLHSNGI-TYLYWYQQKPGQAPRLLIYQ MSNLAS-GIPDRFSGSGSGTDFTLTISRLEPEDFAVYY-CAQNLELPWTFGQGTKVEI KR 1044 heavy chain variable region after CDR transplantation (mouse monoclonal antibody amino acids retained at site VH74) (SEQ ID NO: 2)
QVQLVQSGAEVKKPGSSVKVSCKASGGTFSNY-WIDWVRQAPGQGLEWMGEILP GSGGT-DYNEKFKGRVTITADTSTSTAYMELSSLRSED-TAVYYCARDDYDVFAY WGQGTLVTVSS 1044 humanized antibody light chain variable region (mouse monoclonal antibody amino acids retained at sites VL1, VL4 and VL69) (SEQ ID NO: 3)
DIVMTQSPGTLSLSPGERATLSCRSSKSLLHSNGI-TYLYWYQQKPGQAPRLLIYQ MSNLAS-GIPDRFSSSGSGTDFTLTISRLEPEDFAVYYCAQN-LELPWTFGQGTKVEI KR 1044 humanized antibody heavy chain variable region (mouse monoclonal antibody amino acids retained at sites VH38 and VH74) (SEQ ID NO: 4)
QVQLVQSGAEVKKPGSSVKVSCKASGGTGSNY-WIDWVKQAPGQGLEWMGEILP GSGGT-DYNEKFKGRVTITADTSTSTAYMELSSLRSED-TAVYYCARDDYDVFAY WGQGTLVTVSS In another preferred embodiment, the constant region of the humanized antibody is the same as the constant region of the anti-HER3 mouse monoclonal antibody 1044 (Application No. 2014104015453).

In another preferred embodiment, the sequence with at least one amino acid added, deleted, modified and/or substituted in any of the above amino acid sequences is preferably an amino acid sequence having a homology of at least 80%, more preferably at least 85%, more preferably at least 90%, most preferably at least 95% to the above amino acid sequence.

The antibody of the present invention may be a double-chain or single-chain antibody, and may be preferably a fully humanized antibody.

The antibody derivatives of the present invention may be single chain antibodies, and/or antibody fragments, such as: Fab, Fab', (Fab')$_2$ or other known antibody derivatives in the art, etc., as well as any one or several of IgA, IgD, IgE, IgG and IgM antibodies or other subtypes.

The antibody of the present invention may be a humanized antibody, a CDR grafted and/or modified antibody targeting human HER3.

In the above content of the present invention, the number of added, deleted, modified and/or substituted amino acids is preferably not more than 40% of the total number of amino acids in the original amino acid sequence, more preferably not more than 35%, more preferably 1-33%, more preferably 5-30%, more preferably 10-25%, more preferably 15-20%.

In the present invention, the HER3 mouse monoclonal antibody was successfully humanized, and the humanized antibody can achieve an affinity similar to that of the chimeric antibody. Through preliminary studies on the solubility and endogenous fluorescence of the humanized antibody, it was confirmed that the humanized antibody has preliminary druggability, and is promising to be further developed into humanized monoclonal antibody drugs for targeted therapy in the future.

Preparation of Antibodies

Any method suitable for producing monoclonal antibodies can be used to produce the HER3 antibodies of the present invention. For example, an animal can be immunized with a linked or naturally occurring HER3 protein or fragment thereof. Suitable immunization methods can be used, including adjuvants, immunostimulants, repeated booster immunizations, and one or more approaches can be used.

Any suitable form of HER3 can be used as an immunogen (antigen) to produce non-human antibodies specific for HER3 and to screen the biological activity of the antibody. The immunogen can be used alone or in combination with one or more immunogenicity enhancers known in the art. The immunogen can be purified from natural sources or produced in genetically modified cells. DNA encoding an immunogen may be of genomic origin or non-genomic origin (e.g. cDNA). Appropriate genetic vectors can be used to express the DNA encoding the immunogen, including but not limited to adenovirus vectors, baculovirus vectors, plasmids and non-viral vectors.

Humanized antibodies can be selected from any kind of immunoglobulin, including IgM, IgD, IgG, IgA and IgE. Likewise, any type of light chain can be used in the compounds and methods herein. Specifically, the κ, λ chain or variants thereof can be used in the compounds and methods of the present invention.

An exemplary method of humanizing the HER3 antibody of the present invention is described in Example 1.

The sequence of the DNA molecule for the antibody or a fragment thereof according to the present invention can be obtained by conventional techniques, for example, methods such as PCR amplification or genomic library screening. In addition, the sequences encoding light chain and heavy chain can be fused together, to form a single-chain antibody.

Once a relevant sequence is obtained, recombination methods can be used to obtain the relevant sequence in large quantities. This is usually carried out by cloning the sequence into a vector, transforming a cell with the vector, and then separating the relevant sequence from the proliferated host cell by conventional methods.

In addition, a relevant sequence can be synthesized artificially, especially when the fragment is short in length. Usually, several small fragments are synthesized first, and then are linked together to obtain a fragment with a long sequence. Then, the DNA sequence can be introduced into various existing DNA molecules (or, for example, vectors) and cells known in the art.

The term "nucleic acid molecule" refers to the a DNA molecule or an RNA molecule. The nucleic acid molecule can be single-stranded or double-stranded, but is preferably double-stranded DNA. When a nucleic acid is placed in a functional relationship with another nucleic acid sequence, the nucleic acid is "efficiently linked". For example, if a promoter or enhancer affects the transcription of a coding sequence, the promoter or enhancer is effectively linked to the coding sequence.

The term "vector" refers to a nucleic acid molecule capable of transporting another nucleic acid to which it has been linked. In one embodiment, the vector is "a plasmid", which refers to a circular double-stranded DNA loop into which additional DNA segments can be ligated.

The present invention further relates to a vector comprising said suitable DNA sequence and a suitable promoter or a control sequence. These vectors can be used to transform suitable host cells to enable them to express protein.

The term "host cell" refers to a cell into which an expression vector has been introduced. The host cell can be a prokaryotic cell, such as a bacterial cell; or a lower eukaryotic cell, such as a yeast cell; or a higher eukaryotic cell, such as a plant cell or an animal cell (such as a mammalian cell).

The step of transforming host cells with recombinant DNA as described in the present invention can be carried out by techniques well known in the art. The obtained transformant can be cultured by conventional methods, and the transformant expresses the polypeptide encoded by the gene of the present invention. According to the host cell used, it is cultured in a conventional medium under suitable conditions.

In general, under conditions suitable for expression of the antibody according to the present invention, the host cell obtained is cultured. Then, the antibody according to the present invention is purified by using conventional immunoglobulin purification steps, for example, the conventional separation and purification means well known to those skilled in the art, such as protein A-Sepharose, hydroxyapatite chromatography, gel electrophoresis, dialysis, ion exchange chromatography, hydrophobic chromatography, molecular sieve chromatography or affinity chromatography.

The monoclonal antibody obtained can be identified by conventional means. For example, the binding specificity of a monoclonal antibody can be determined by immunoprecipitation or an in vitro binding assay (such as radioimmunoassay (RIA) or enzyme-linked immunosorbent assay (ELISA)).

Antibody Preparation

Antibodies have different stability in different preparation buffers, manifested by changes in charge heterogeneity, degradation and polymerization of antibody molecules, etc. These changes in quality properties are related to the physical and chemical properties of the antibody itself. Therefore, in the development of antibody drugs, it is necessary to screen suitable preparation buffers according to the physical and chemical properties of different antibodies. Currently commonly used antibody preparation buffer systems include phosphate buffer, citrate buffer, histidine buffer, etc., and different concentrations of salt ions or excipients such as sorbitol, trehalose, and sucrose are added according to the property of the antibody, and an appropriate amount of surfactants such as Tween 20 or Tween 80 is added to maintain the stability of the antibody.

The antibody preparation of the present invention is as described in the seventh aspect of the present invention.

The antibody drug combination preparation of the present invention can effectively inhibit side reactions such as aggregation, precipitation, hydrolysis, oxidation, and deamidation of the humanized antibody of the present invention, and can effectively improve the product stability under conditions of compression (high temperature, strong light irradiation and freeze-thaw etc.), acceleration and long-term cold storage.

Pharmaceutical Composition

The present invention further provides a composition. In the preferred embodiments, the composition is a pharmaceutical composition comprising the antibody, or an active fragment, a fusion protein or an ADC thereof, or a corresponding CAR-T cell, and a pharmaceutically acceptable carrier. In general, these substances may be formulated in a non-toxic, inert and pharmaceutically acceptable aqueous carrier medium, wherein the pH is generally about 5-8, preferably, pH is about 6-8, though the pH value may be varied depending on the nature of the substances to be formulated and the condition to be treated. The formulated pharmaceutical composition may be administered by conventional routes, including (but not limited to): intratumoral, intraperitoneal, intravenous, or topical administration.

The antibody of the present invention can also be used for cell therapy by expressing the nucleotide sequence in the cell. For example, the antibody is used for chimeric antigen receptor T cell immunotherapy (CAR-T) and the like.

The pharmaceutical composition according to the present invention can be directly used for binding to a HER3 protein molecule, and thus can be used for preventing and treating HER3 related diseases. In addition, other therapeutic agents can also be used at the same time.

The pharmaceutical composition according to the present invention comprises a safe and effective amount (e.g. 0.001-99 wt %, preferably 0.01-90 wt %, preferably 0.1-80 wt %) of the monoclonal antibody according to the present invention (or a conjugate thereof) and a pharmaceutically acceptable carrier or excipient. Such carriers include (but are not limited to): saline, buffers, glucose, water, glycerol, ethanol, and a combination thereof. Pharmaceutical preparations should correspond to the administration modes. The pharmaceutical composition according to the present invention can be prepared in the form of an injection, for example, by a conventional method using physiological saline or an aqueous solution containing glucose and other adjuvants. A pharmaceutical composition, for example, an injection and a solution, should be prepared under aseptic conditions. The administration amount of an active ingredient is a therapeutically effective amount, for example, about 1 μg per kilogram of body weight to about 5 mg per kilogram of body weight daily. In addition, the polypeptide according to the present invention may also be used in combination with an additional therapeutic agent.

When a pharmaceutical composition is used, a safe and effective amount of pharmaceutical composition is administered to a mammal, wherein the safe and effective amount is generally at least about 10 μg per kilogram of body weight, and in most cases, no more than about 50 mg per kilogram of body weight, preferably, the amount is from about 10 μs per kilogram of body weight to about 20 mg per kilogram of body weight. Of course, a specific amount should also depend on the factors such as administration route and physical conditions of a patient, which fall into the skills of skilled physicians.

Use for Detection and the Kit

The antibody of the present invention can be used for detection, for example, for detection of samples to provide diagnostic information.

In the present invention, the specimens (samples) used include cells, tissue samples and biopsy specimens. The term "biopsy" used in the present invention shall include all kinds of biopsy known to those skilled in the art. Therefore, the biopsy used in the present invention may include, for example, tissue samples prepared by endoscopic methods or organ puncture or needle biopsy.

The samples used in the present invention include fixed or preserved cells or tissue samples.

The present invention also provides a kit containing the antibody (or a fragment thereof) of the present invention. In a preferred embodiment of the present invention, the kit further includes a container, instructions for use, buffer, and the like. In a preferred embodiment, the antibody of the present invention can be immobilized on a detection plate.

The Main Advantages of the Present Invention (a) The humanized antibody of the present invention has a typical tryptophan and tyrosine embedded structure. The selected human VH, VL framework template has a stable structure and is compatible with the mouse monoclonal antibody CDR region. The variable regions of the light and heavy chains can pair together well, with high affinity and forming a stable structure.

(b) Compared with chimeric antibodies, the humanized antibody of the present invention has excellent biological activity and specificity. While retaining the affinity equivalent to HER3, it has lower immunogenicity and higher amount of expression.

(c) The humanized antibody of the present invention has high solubility and good druggability.

(d) The humanized antibody of the present invention shows obvious tumor growth inhibition properties in the A549 tumor model, and the tumor growth inhibitory activity is related to the administration dose, which proves that the humanized anti-HER3 monoclonal antibody still have good biological activity.

(e) Compared with mature antibodies, the present invention takes into account the similarity and human use frequency when selecting humanized framework regions. The humanized antibodies have lower immunogenicity and higher expression levels (especially in mammalian cells, such as in CHO-K1 cells), more stable structure, and better druggability.

(f) The stability of the humanized antibody of the present invention in the antibody preparation of the present invention is very good.

(g) The humanized antibody of the present invention was constructed in CHO-K1 cells for stable expression cell lines, and the selected stable cell lines were cultured in Fed Batch in shake flasks, and the antibody expression amount reached 4-5 g/L.

The invention is further illustrated below in conjunction with specific embodiments. It should be understood that the examples are not intended to limit the scope of the invention. The experimental methods in the following examples which do not specify the specific conditions are usually in accordance with conventional conditions, such as conditions described in Sambrook et al., Molecular Cloning: Laboratory Manual (New York: Cold Spring Harbor Laboratory Press, 1989), or in accordance with the conditions recommended by the manufacturer. Unless otherwise stated, percentages and parts are by weight.

Experiments with no specific conditions specified in the examples or test examples of the present invention are usually carried out under conventional conditions, or according to the conditions recommended by the raw material/commodity manufacturer. Reagents without specific sources are the conventional reagents purchased on the market.

Materials and Methods

1. Strains, Cells, Plasmids and Experimental Animals

E. coli DH5α competent cells were prepared by our laboratory. FreeStyle 293-F cells and expression medium were purchased from Gibco. pSGHV0 eukaryotic expression plasmid was gifted by Dr. D. J. Leahy from Department of Biophysics, School of Medicine, Johns Hopkins University, USA. Babl/c nude mice were purchased from Shanghai Slack Laboratory Animal Co., Ltd.

2. Main Reagents and Equipments

The site-directed mutagenesis kit was purchased from Beijing Saibaisheng Gene Technology Co., Ltd. Mabselect Sure affinity medium was purchased from GE company. Rituximab (lot number H0709) and trastuzumab (lot number N3674) were purchased from Shanghai Roche Pharmaceutical Co., Ltd. HER3 extracellular domain recombinant protein was recombinantly expressed by CHO cells. Goat anti-human antibody was purchased from Jackson ImmunoResearch. Polyethylenimine (PEI MW 25000) was purchased from Polysciences. Polyethylene glycol 8000 (PEG 8000) was purchased from Sigma-Aldrich. SDS-MW Analysis Kit was purchased from Beckman Coulter. OPM-CHO CD07, PFF05 and CDF16 culture medium were purchased from Shanghai Optima Biotechnology Co., Ltd. 1044 mouse monoclonal antibody was the antibody 1044 in 2014104015453.

3. Humanized Antibody Construction

After the 1044 mouse monoclonal antibody CDR was transplanted to the human antibody framework, the humanized variable region gene sequences were synthesized by Shanghai Boshang Biotechnology Co., Ltd., and then the heavy chain and light chain variable region genes were constructed to the pSGHV0 vector containing human IgG1 heavy chain constant region and κ chain constant region. The sites of VH38, VH48, VH68, VL69 in humanized antibody framework regions were backmutated using a site-directed mutagenesis kit, and confirmed by sequencing. 1044 human-mouse chimeric antibody and each back-mutant humanized antibody were transiently transfected with PEI in 293F cells, and the affinity of transiently transfected cell culture supernatant was measured with ProteOn XPR36 after centrifugation at 2000 rpm. The final selected humanized antibody sequences were obtained by Shanghai Optima Biotech Co., Ltd. CHO-K1 stable cell line was constructed, and the stable cell line was used to express the humanized antibody hu1044. The screened stable cell line was Fed Batch cultured in a shake flask, inoculated into a culture flask at a cell density of $5 \times 10^5$/ml. The basic medium was OPM-CHO CD07. On the 3rd, 5th, 7th, 9th, and 11th day of culture, PFF05 supplementary medium was added with a volume of 3%, 5%, 7%, 5% and 3% of the culture volume, and on the 5th, 7th, 9th, and 11th day of culture, CDF16 supplementary medium was added with a volume of 0.3% of the culture volume. Wherein, the glucose content was maintained at 2-6 g/L. When the cell viability rate was less than 60% or the culture lasted 15 days, the culture was finished. The antibody expression level reached 4-5 g/L. Then the humanized antibody was obtained by purification by Mabselect Sure Protein A affinity medium, and the purified antibody was concentrated to 60 mg/mL.

4. Antibody Affinity Measurement Using ProteOn XPR36 Protein Interaction Array System GLM chip horizontal 6 channels were labelled with goat anti-human antibodies, and after the channels were turned 90 degrees into a vertical position, it captured chimeric antibodies or humanized antibodies expressed by 293F cells. And the channels were turned to horizontal position, and Channels 1-5 were injected with 20 nM, 10 nM, 5 nM, 2.5 nM, 1.25 nM of samples of HER3 extracellular domain protein respectively, and Channel 6 was injected with buffer. 5 kinetic response curves were obtained, respectively representing the results of the reaction between different concentrations of antigen and the captured antibody. The Langmuir model was used to calculate the affinity constants KD (M) of each chimeric antibody and humanized antibody mutant.

5. Antibody Solubility Measurement by PEG Precipitation Method

FB1 solution (90 g of sodium chloride, 73.5 g of trisodium citrate, and 7 g of polysorbate 80 were dissolved in 1 L water for injection, and pH was adjusted to 6.5) and FB2 buffer (0.3 g of histidine, 0.5 g of histidine hydrochloride, 0.08 g of polysorbate 20, and 18.9 g of trehalose were dissolved in 1 L water for injection, and pH was adjusted to 6.0) were prepared. Deionized water was used to prepare two stocks of 40% PEG 8000, wherein the pH were adjusted to 6.5 and 6.0 respectively, and then FB1 and FB2 were used to dilute the 40% PEG 8000 respectively to different concentrations. The 60 mg/mL HER3 humanized antibody were replaced with an ultrafiltration tube into the FB1 and FB1 buffers respectively, with a replacement volume of 100 times, and the final concentrations were both 20 mg/mL. Then rituximab, trastuzumab, HER3 humanized monoclonal antibody (FB1), HER3 humanized monoclonal antibody (FB1) were diluted to 10 mg/mL with respective buffers, wherein 100 μL of each antibody was taken and mixed with 100 μL of different concentrations of PEG 8000 (5%, 10%, 15%, 20%, 25%, 30%, 35%, 40%) well in a 96 well plate, and the results were observed after 10 minutes of reaction.

6. Non-Reduced Capillary Electrophoresis Detection (CE-SDS)

100 μg sample was taken, added with 70 μL SDS sample buffer to make a final volume of 95 μL, then added with 5 μL of 250 mM iodoacetamide and mixed well. The mixture was centrifuged for 1 minute at 5000 rpm, and bathed in water at 65° C. for 4 minutes. After cooled to room temperature, the solution was centrifuged for 1 minute at 5000 rpm, taken with 100 μL into the capillary electrophoresis injection bottle for analysis. Uncoated-Fused Silica Capillary (inner diameter 50 μm), with an effective length of 24.5 cm was used. The sampling was conducted by 5 kV reverse polarity motorized sampling for 20 s, with a separation voltage of 15 kV, a separation time of 40 min, and a detection wavelength of 220 nm.

7. Ion Exchange High Performance Liquid Chromatography (IEX-HPLC)

Mobile Phase A: 10 mM Sodium Phosphate Solution, pH 7.4; Mobile Phase B: 10 mM Sodium Phosphate Solution, 0.25 M Sodium Chloride, pH 7.4; Column: Propac WCX-10 (4.0×250 mm) from Dionex; Detector: ultraviolet detector, wavelength 280 nm; Column temperature: 35° C.; Injection volume: 40 μg; Flow rate: 0.5 mL/min; Separation gradient: mobile phase B was increased from 0% to 30% within 27 min; Collection time: 41 min.

8. Size Exclusion High Performance Liquid Chromatography (SEC-HPLC)

Mobile phase: 0.2 M sodium phosphate buffer, pH 6.8; Column: Super SW 3000 (4.6×300 mm, 4 μm) from TOSOH Bioscience; Detector: UV detector, wavelength 280 nm;

Flow rate: 0.35 mL/min; Column temperature: 30° C.; Injection volume: 30 μg; Collection time: 20 min.

9. Endogenous Fluorescence Detection

The samples were diluted with their respective buffers to 1.0 mg/mL, added into a cuvette and detected on the SpectraMax M5, wherein the excitation wavelength was 295 nm, and the emission wavelength was scanned from 310 nm to 450 nm with a scan step of 1 nm.

10. Humanized Antibody Efficacy Tested In Vivo

Human non-small cell lung cancer cells A549 were cultured to the logarithmic growth phase, digested with trypsin, and washed with serum-free medium, and inoculated subcutaneously with the amount of 1×10⁷ cells to the back of 3-4 weeks old Babl/c nude mice. Two weeks later, when obvious tumors were seen, the nude mice were randomly grouped, with 6 mice in each group. The concentrations of HER3 humanized monoclonal antibody administered were: 30 mg/kg, 15 mg/kg, 7.5 mg/kg, with PBS as the control, by intraperitoneal injection. Treatments were conducted twice a week, and tumor volumes were measured twice a week. Nude mouse tumor volume: $V=0.5 \times a \times b^2$, wherein a is the long diameter of the tumor, and b is the short diameter of the tumor.

11. Humanized Antibody Preparation Formulation Screening 11.1 Preparation Formulation Screening I The following three buffers were prepared: citrate buffer (containing 25 mM of sodium citrate, 140 mM of sodium chloride and 0.07% of Tween-80, pH6.5), phosphate buffer (containing 50 mM of phosphate, 140 mM of sodium chloride and 0.07% of Tween-80, pH8.0), and histidine buffer (containing 2 mM of histidine, 2 mM of histidine hydrochloride, 1.5% of trehalose and 0.07% of Tween-80, pH6.0). The purified humanized antibody was replaced into the above three buffers, to a final concentration of 40 mg/mL. After standing at −70° C., 2-8 □ and 37° C. for one week, the changes of charge heterogeneity were detected by IEX-HPLC method.

11.2 Preparation Formulation Screening II

The following two buffers were prepared: citrate buffer (containing 25 mM of sodium citrate, 140 mM of sodium chloride and 0.07% of Tween-80, pH6.5), and histidine buffer (containing 2 mM of histidine, 2 mM of histidine hydrochloride and 0.07% of Tween-80, pH6.0). 1.5% trehalose or 2% sorbitol were added to these two buffers respectively, and then the purified humanized antibodies were replaced into the above buffers respectively, to a final concentration of 40 mg/mL. After standing at 37° C. for one week, the mass changes were detected by IEX-HPLC and SEC-HPLC methods.

11.3 Preparation Formulation Screening □II

Histidine buffer (containing 2 mM histidine, 2 mM histidine hydrochloride and 0.07% Tween-80, pH6.0) was prepared, respectively added with 25, 50, 75, 125, 150 mM of sodium chloride. And then the humanized antibody was replaced into the above buffers with different salt ions, with a final concentration of 40 mg/mL. The influence of salt ions on the turbidity of the antibody was observed.

The humanized antibody was prepared in histidine buffer (containing 2 mM of histidine, 2 mM of histidine hydrochloride and 0.07% of Tween-80, pH6.0) to 40 mg/mL. After standing at 37 □ for two weeks, the mass changes were measured using IEX-HPLC method, SEC-HPLC method and non-reduced CE-SDS method.

Example 1 Antibody Humanization

After a large number of experimental screenings, human IGKV3-20*01 amino acid sequences were finally selected as the templates for humanization of the light chain, and human IGHV1-69*01 amino acid sequences were selected as the templates for humanization of the heavy chain. Mouse monoclonal antibody 1044 light and heavy chain CDR regions were transplanted to human template framework regions. Mouse monoclonal antibody Jκ region was replaced by human Jκ1 sequence, and mouse monoclonal antibody JH region was replaced by human JH4 sequence. Sequence alignment between the framework regions of mouse monoclonal antibody and human Germline was shown in FIG. 1. SEQ ID NO: 1 was obtained by retaining the mouse VL1 and VL4 amino acids on the basis of SEQ ID NO: 9; SEQ ID NO: 2 was obtained by retaining the mouse VH74 amino acid on the basis of SEQ ID NO: 10.

Wherein, the sequences of the light chain variable region and the heavy chain variable region of the mouse monoclonal antibody 1044 were shown in SEQ ID NO: 5 and 6, respectively.

1044 mouse monoclonal antibody light chain variable region (SEQ ID NO: 5)
DIVMTQAAFSNPVTLGTSASISCRSSKSLLHSNGI-TYLYWYLQKPGQSPQLLI YQMSN-LASGVPDRFSSSGSGTDFTLRISRVEAEDVGVYY-CAQNLELPWTFGGGT KLEIKR 1044 mouse monoclonal antibody heavy chain variable region (SEQ ID NO: 6)
EVQLQQSGTELMKPGASVKISCKATGGTFSNY-WIDWVKQRPGHGLEWIGEI LPGSGGT-DYNEKFKGKATFTADTSSNTAYMQLSSLTSED-SAVYYCARDDYDVFA YWGQGTLVTVSA As shown in FIG. 1, the sequences of h_VL and h_VH after CDR transplantation were shown in SEQ ID NO: 9 and 10.

1044 light chain variable region after CDR transplantation (SEQ ID NO: 9)
EIVLTQSPGTLSLSPGERATLSCRSSKSLLHSNGITY-LYWYQQKPGQAPRLLIYQM SNLAS-GIPDRFSGSGSGTDFTLTISRLEPEDFAVYY-CAQNLELPWTFGQGTKVEIKR 1044 heavy chain variable region after CDR transplantation (SEQ ID NO: 10)
QVQLVQSGAEVKKPGSSVKVSCKASGGTFSNY-WIDWVRQAPGQGLEWMGEILP GSGGT-DYNEKFKGRVTITADESTSTAYMELSSLRSED-TAVYYCARDDYDVFAY WGQGTLVTVSS At the same time, 3 sites (VL1 site, VL4 site and VH74 site) from original mouse monoclonal antibody were retained during the CDR transplantation process, thus obtaining the humanized antibody h1044-0, wherein the sequences of the light chain variable region and heavy chain variable region of the antibody were shown in SEQ ID NO: 1 and 2, respectively.

1044 light chain variable region after CDR transplantation (mouse monoclonal antibody amino acids retained at sites VL1, VL4) (SEQ ID NO: 1)
DIVMTQSPGTLSLSPGERATLSCRSSKSLLHSNGI-TYLYWYQQKPGQAPRLLIYQ MSNLAS-GIPDRFSGSGSGTDFTLTISRLEPEDFAVYY-CAQNLELPWTFGQGTKVEI KR 1044 heavy chain variable region after CDR transplantation (mouse monoclonal antibody amino acids retained at site VH74) (SEQ ID NO: 2)
QVQLVQSGAEVKKPGSSVKVSCKASGGTFSNY-WIDWVRQAPGQGLEWMGEILP GSGGT-DYNEKFKGRVTITADTSTSTAYMELSSLRSED-TAVYYCARDDYDVFAY WGQGTLVTVSS The results were shown in Table 1, the affinity of humanized h1044-0 antibody after CDR transplantation with HER3 protein was about 32 times lower than that of the chimeric antibody. In addition, back mutation studies were performed on some sites in the framework region, including: VH1 mutated from Gln to Glu, VH25 mutated from Ser to Thr, VH76 mutated from Thr to Ser, and VH77 mutated from Ser to Asn. No significant increase in affinity of humanized antibodies was found.

TABLE 1

The affinities to HER3 of the chimeric antibody and humanized antibodies after CDR transplantation

| Antibody | Ka (1/Ms) | Kd (1/s) | KD (M) |
|---|---|---|---|
| Chimeric antibody | 8.74E+06 | 2.29E−04 | 2.62E−10 |
| h1044-0 | 5.03E+05 | 4.27E−03 | 8.48E−9 |
| VH1 back mutation | 4.18E+05 | 3.82E−03 | 9.14E−9 |
| VH25 back mutation | 5.25E+05 | 3.17E−03 | 6.02E−9 |
| VH76 back mutation | 5.31E+05 | 3.44E−03 | 6.49E−9 |
| VH77 back mutation | 4.63E+05 | 3.27E−03 | 7.07E−9 |

Further, the humanized antibody h1044-0 was mutated. VL69 back mutation was the mutation at a position corresponding to position 69 in SEQ ID NO: 1 from Gly to Ser, wherein the affinity was significantly improved, to about 2 times different from the chimeric antibody.

On this basis, VH38, VH48 or VH68 site mutations (VH38 mutated from Arg to Lys, VH48 mutated from Met to Ile, and VH68 mutated from Val to Ala) were conducted. After the mutations, the affinity of the humanized antibodies were significantly improved, basically close to that of the chimeric antibody, and restored to within 2 times the affinity constant of the chimeric antibody. The sequences after VL69, VH38 back mutations meet the requirements of humanization. In addition, when the VL63/69 back mutation (VL63 back mutated from Ile to Val, VL69 back mutated from Gly to Ser) was combined with VH38 mutation (VH38 back mutated from Arg to Lys), VH68 mutation (VH68 back mutated from Val to Ala) and VH67/68 mutation (VH67 back mutated from Arg to Lys, and VH68 back mutated from Val to Ala), the affinity was also close to that of the chimeric antibody, see Table 2. The sequences after VL69, VH38 back mutated were used as the final humanized antibody hu1044 (the light chain variable region and heavy chain variable region sequences were shown in SEQ ID NO: 3 and 4, respectively).

TABLE 2

The affinities to HER3 of the chimeric antibody and humanized antibodies after back mutation

| Antibody | Ka (1/Ms) | Kd (1/s) | KD (M) |
|---|---|---|---|
| Chimeric antibody | 1.05E+06 | 2.93E−04 | 2.78E−10 |
| VL69 back mutation (hu1044-1) | 8.43E+05 | 5.02E−04 | 5.95E−10 |
| VL69, VH38 back mutation (hu1044) | 8.75E+05 | 3.86E−04 | 4.42E−10 |
| VL69, VH48 back mutation (hu1044-3) | 8.82E+05 | 4.94E−04 | 5.54E−10 |
| VL69, VH68 back mutation (hu1044-4) | 8.41E+05 | 3.88E−04 | 4.61E−10 |
| VL63/69, VH38 back mutation (hu1044-5) | 8.44E+05 | 3.53E−04 | 4.19E−10 |
| VL63/69, VH68 back mutation (hu1044-6) | 9.04E+05 | 3.80E−04 | 4.20E−10 |
| VL63/69, VH67/68 back mutation (hu1044-7) | 1.00E+06 | 3.76E−04 | 3.75E−10 |

"VL69 back mutation" refers to the mutation from Gly to Ser at position VL69 corresponding to the position in SEQ ID NO: 1 (the mutated sequence is shown in SEQ ID NO: 3).

"VL63/VL69 back mutation" refers to the mutation from Ile to Val at position VL63 and the mutation from Gly to Ser at position VL69 corresponding to the positions in SEQ ID NO: 1 (the mutated sequence is shown in SEQ ID NO: 7).

DIVMTQSPGTLSLSPGERATLSCRSSKSLLHSNGI-TYLYWYQQKPGQAPRLLIYQ MSN-LASGVPDRFSSSGSGTDFTLTISRLEPEDFAVYY-CAQNLELPWTFGQGTKVEI KR (SEQ ID NO: 7)

"VH38 back mutation" refers to the back mutation from Arg to Lys at position VH38 corresponding to the position in SEQ ID NO: 2 (the mutated sequence is shown in SEQ ID NO: 4).

"VH48 back mutation" refers to the mutation from Met to Ile at position VH48 corresponding to the position in SEQ ID NO: 2.

"VH68 back mutation" refers to the back mutation from Val to Ala at position VH68 corresponding to the position in SEQ ID NO: 2.

"VH67/VH68 back mutation" refers to the back mutation from Arg to Lys at position VH67 and the back mutation from Val to Ala at position VH68 corresponding to the positions in SEQ ID NO: 2 (SEQ ID NO: 8).

QVQLVQSGAEVKKPGSSVKVSCKASGGTFSNY-WIDWVRQAPGQGLEWMGEILP GSGGT-DYNEKFKGKATITADTSTSTAYMELSSLRSED-TAVYYCARDDYDVFAY WGQGTLVTVSS (SEQ ID NO: 8)

Example 2 Solubility Analysis of Humanized Antibodies

Generally, the dosage of antibody drugs used in the human body is relatively large, and only antibody molecules with high solubility can have a certain degree of druggability. Solubility is not only related to the physical and chemical properties of the antibody, such as isoelectric point, surface hydrophobicity, binding force between light and heavy chains, etc., but also related to the buffer system where the antibody is dissolved.

PEG precipitation method can be used to detect the solubility of proteins. Humanized antibody hu1044 after VL69, VH38 back mutation was recombinantly expressed in CHO-K1 cells. And after Protein A affinity chromatography, the antibody was placed into different buffer systems by ultrafiltration. FB1 was the buffer of rituximab preparation, and FB2 was the buffer of trastuzumab. Using PEG precipitation method, it can be seen that in the FB1 buffer, the humanized antibody hu1044 began to precipitate under the 5% PEG condition, and in the FB2 buffer, the humanized antibody hu1044 began to precipitate under the 10% PEG condition, see FIG. 2.

Compared with the FB1 buffer, the HER3 humanized antibody hu1044 had significantly higher solubility in the FB2 buffer. The solubility of HER3 humanized antibody hu1044 in the FB2 buffer was higher than that of rituximab control, but was lower than that of trastuzumab control. In non-reducing capillary electrophoresis, the purity of the HER3 humanized antibody hu1044 was significantly reduced and the polymers were increased after ultrafiltration and replacement in the FB1 buffer, while the purity did not significantly change after the ultrafiltration and replacement in the FB2 buffer. It was further confirmed that the HER3 humanized antibody hu1044 had better solubility in FB2, see Table 3. The HER3 humanized antibody hu1044 showed different solubilities in different buffer systems, and its solubility in the FB2 buffer was better than that in FB1, and better than that of rituximab.

TABLE 3

Non-reducing capillary electrophoresis detection results of HER3 hu1044 humanized antibody

| Humanized antibody hu1044 | Low molecular weight impurities | IgG main peak | High molecular weight impurities |
|---|---|---|---|
| Control without ultrafiltration replacement of buffer | 2.84% | 97.16% | 0 |
| Ultrafiltration replacement to FB1 | 2.69% | 73.22% | 24.10% |
| Ultrafiltration replacement to FB2 | 2.28% | 97.73% | 0 |

Example 3 Endogenous Fluorescence Analysis of Humanized Antibody Hu1044

Tryptophan and tyrosine in protein molecules emit fluorescence under suitable excitation luminescence, especially that tryptophan has strong autofluorescence. Tryptophan and tyrosine are sensitive to changes in the protein microenvironment. When tryptophan and tyrosine are exposed on the surface of the protein from the hydrophobic center of the protein, the fluorescence spectrum will undergo red shift. Detection of protein endogenous fluorescence can determine the stability of protein structure. The maximum emission wavelength of antibody endogenous fluorescence $\lambda$max can reflect the spatial distribution of tryptophan and tyrosine in antibody molecules. The tryptophans and tyrosines of VL35W, VL86Y, VH36W, VH90Y, and VH103W were very conserved in the framework region of the antibody molecule, and they were embedded in the hydrophobic center.

The results were shown in FIG. 3. By comparing the endogenous fluorescences of HER3 humanized antibody hu1044 and those of trastuzumab and rituzumab, it can be seen that the maximum emission wavelength of HER3 humanized monoclonal antibody hu1044 $\lambda$max was 335 nm, while the $\lambda$max of trastuzumab was 337 nm and the $\lambda$max of rituximab was 348 nm. The $\lambda$max values of HER3 humanized antibody hu1044 and trastuzumab were similar, and both of them had a typical structure with tryptophan well embedded, while rituximab behaved slightly worse. The $\lambda$max value of HER3 humanized antibody hu1044 was similar to that of trastuzumab, and it had a typical structure with tryptophan and tyrosine well embedded, which confirmed that the human VH and VL framework templates selected in the humanization process were stable and fit well with the mouse monoclonal antibody CDR regions, and the variable regions of the light and heavy chains can be matched well together.

Example 4 Efficacy of Humanized Antibody in Animals

1. Non-Small Cell Lung Cancer Cells A549 Model

Human non-small cell lung cancer cells A549 were cultured to the logarithmic growth phase, digested with trypsin, and washed with serum-free medium, and inoculated subcutaneously with the amount of $1\times10^7$ cells to the back of 3-4 weeks old Babl/c nude mice. Two weeks later, when obvious tumors were seen, the nude mice were randomly grouped, with 6 mice in each group. The concentrations of HER3 humanized monoclonal antibody hu1044 administered were: 30 mg/kg, 15 mg/kg, 7.5 mg/kg, with PBS as the control, by intraperitoneal injection. Treatments were conducted twice a week, and tumor volumes were measured twice a week. Nude mouse tumor volume: $V=0.5\times a\times b^2$, wherein a is the long diameter of the tumor, and b is the short diameter of the tumor.

Figure 4:
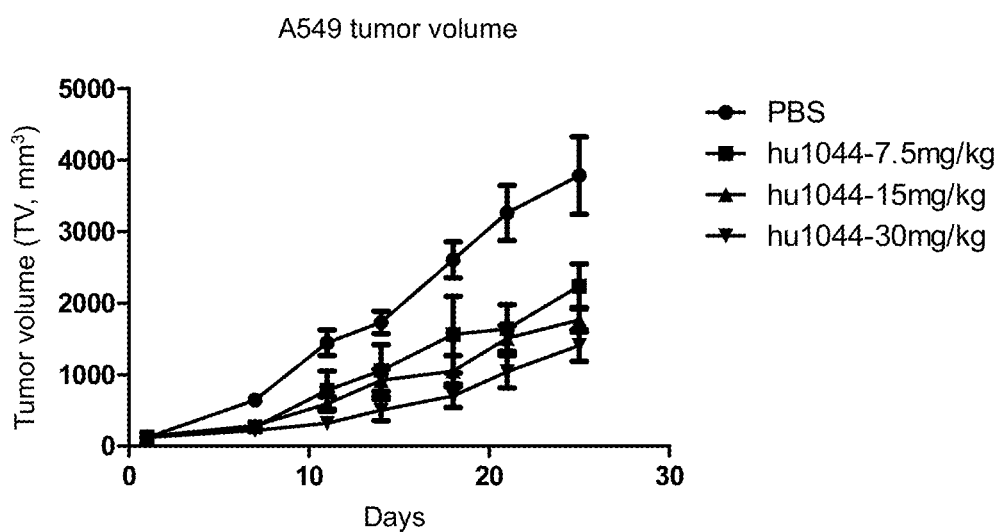
FIG. 4 shows the tumor (A549) in vivo inhibitory effect of the humanized antibody of the present invention.

In the A549 nude mouse tumor model, the humanized antibody hu1044 had a significant inhibitory effect on the growth of the A549 tumor, and the inhibitory effect was related to the administered dose (see FIG. 4). The dose of 30 mg/kg showed the highest inhibition rate, wherein the tumor growth inhibition rate was 63%, confirming that the humanized antibody still had good biological activity and had the potential to treat tumors in vivo.

2. Fadu Model of Human Pharyngeal Squamous Cell Carcinoma

Fadu cells of human pharyngeal squamous cell carcinoma were cultured to the logarithmic growth phase, and the cells were collected after trypsinization, and counted. Nude mice were subcutaneously inoculated with $5\times10^6$ human pharyngeal squamous cell carcinoma Fadu cells. After the average tumor volume grew to 100 mm$^3$, the animals were grouped (D0) according to the tumor volumes, with 6 in each administration group and 12 in the solvent control group. Mice were injected intravenously with HER3 humanized antibody (hu1044-7) twice a week for a total of 4 times, and the administration volume was 10 mL/kg. The dosage of HER3 humanized antibody was 0.2, 0.6, 2 mg/kg. Mice in Erbitux (produced by Merck, a monoclonal antibody for the first-line treatment of recurrent and metastatic head and neck squamous cell carcinoma) control group were given a dose of 0.5 mg/kg. Mice in the solvent group were given the same volume of normal saline. The tumor volumes were measured and mice were weighed twice a week, and the data were recorded. Nude mouse tumor volume: $V=0.5\times a\times b^2$, wherein a is the long diameter of the tumor, and b is the short diameter of the tumor.

Figure 5:
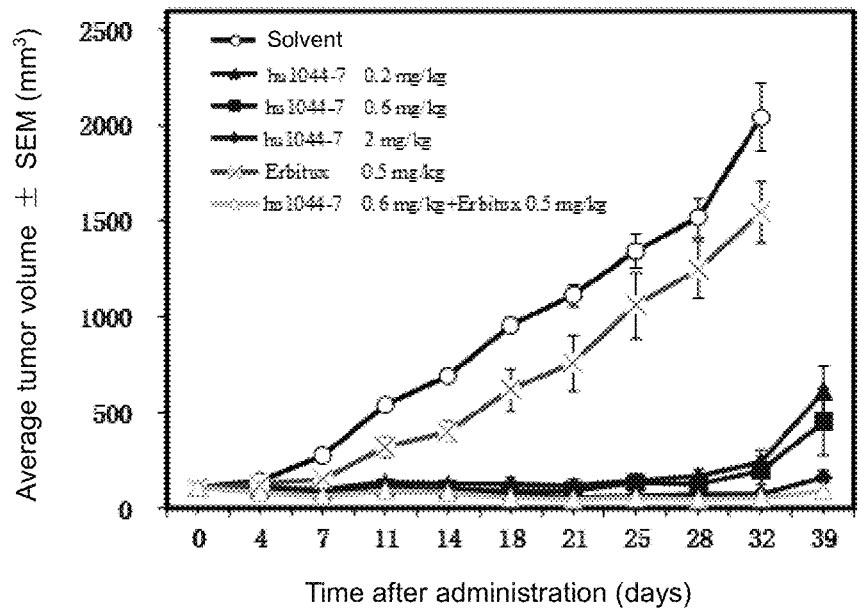
FIG. 5 shows the tumor (Fadu) in vivo inhibitory effect of the humanized antibody hu1044-7 of the present invention.

The results were shown in FIG. 5. Compared with the solvent control group and the Erbitux treatment group, the HER3 humanized antibody administration group showed significant tumor inhibition effects. There were mice in the HER3 humanized antibody treatment group showing partial tumor regression (the tumor volume after treatment was smaller than the tumor volume before treatment), and the tumors of 5 mice in the 2 mg/kg group were regressed partially. The tumors of 6 mice in the HER3 humanized antibody and Erbitux combination treatment group all experienced partial regression (P<0.05, compared with Erbitux monotherapy). Mice in the treatment group tolerated the drugs well, and no symptoms such as weight loss occurred.

3. Breast Cancer BT-474 Model

Human breast cancer BT-474 cells were cultured to the logarithmic growth phase, and the cells were collected after trypsinization, and counted. Nude mice were subcutaneously inoculated with $8 \times 10^6$ human breast cancer BT-474 cells. After the average tumor volume grew to 100-150 mm$^3$, the animals were grouped (D0) according to the tumor volumes, with 6 in each administration group and 12 in the solvent control group. Mice were injected intravenously with HER3 humanized antibody (hu1044-7) twice a week for a total of 6 times, and the administration volume was 10 mL/kg. The dosage of HER3 humanized antibody was 2, 6, 20 mg/kg. Mice in Herceptin (produced by Roche, a monoclonal antibody for the first-line treatment of Her2 positive breast cancer) control group were given a dose of 7.5 mg/kg. Mice in the solvent group were given the same volume of normal saline. The tumor volumes were measured and mice were weighed twice a week, and the data were recorded. Nude mouse tumor volume: $V=0.5 \times a \times b^2$, wherein a is the long diameter of the tumor, and b is the short diameter of the tumor.

Figure 6:
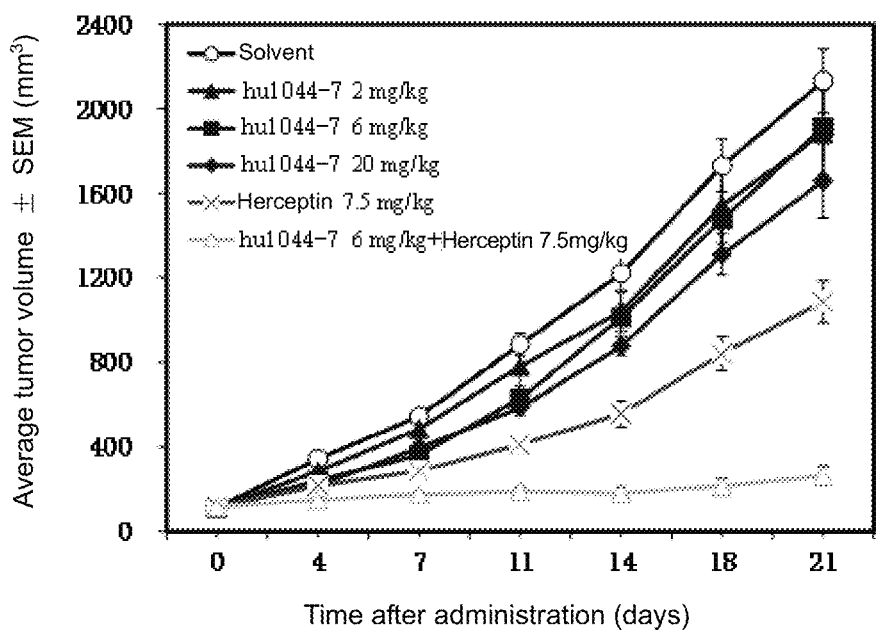
FIG. 6 shows the tumor (BT-474) in vivo inhibitory effect of the humanized antibody hu1044-7 of the present invention.

Results were shown in FIG. 6. Compared with the solvent control group and Herceptin treatment group, in the HER3 humanized antibody and Herceptin combination treatment group, the growth of mouse tumors were significantly inhibited ($P<0.01$, compared with Herceptin monotherapy), indicating a significant synergistic therapeutic effect with Herceptin. Mice in the treatment group tolerated the drugs well, and no symptoms such as weight loss occurred.

Example 5 Humanized Antibody Hu1044
Preparation Formulation Screening

In 25 mM citrate buffer and 2 mM histidine histidine hydrochloride buffer, whether humanized antibody hu1044 was placed at 37 □ or 2-8 □ for one week, the charge isomers were relatively stable, while in phosphate buffer, after placed at 37 □ or 2-8 □ for one week, the charge isomers changed significantly (see Table 4), indicating that the antibody was relatively stable in 25 mM citrate buffer and 2 mM histidine buffer.

TABLE 4

Humanrized antibody hu1044 preparation buffer Screen I

| | | IEX-HPLC | | |
|---|---|---|---|---|
| Buffer | Experimental conditions | Acid peak % | Main Peak % | Alkaline Peak % |
| Citrate buffer | −70 □ for 7 days | 24.32 | 68.33 | 7.36 |
| | 2-8 □ for 7 days | 24.27 | 68.25 | 7.49 |
| | 37 □ for 7 days | 26.27 | 65.82 | 7.92 |
| Phosphate buffer | −70 □ for 7 days | 24.91 | 67.43 | 7.67 |
| | 2-8 □ for 7 days | 43.25 | 50.01 | 6.65 |
| | 37 □ for 7 days | 61.20 | 32.52 | 6.28 |
| Histidine buffer | −70 □ for 7 days | 23.85 | 68.20 | 7.94 |
| | 2-8 □ for 7 days | 24.50 | 67.46 | 8.02 |
| | 37 □ for 7 days | 27.30 | 65.27 | 7.69 |

After the citrate buffer and histidine hydrochloride buffer were added with trehalose or sorbitol, there was no significant difference in antibody charge isomers compared with the test group without trehalose or sorbitol. There was no significant difference in SEC-HPLC purity, either. But in the histidine buffer system, the SEC-HPLC purity was slightly higher than that in the citric acid buffer system, see

TABLE 5

Humanrized antibody hu1044 preparation buffer Screen II

| | | IEX-HPLC | | | |
|---|---|---|---|---|---|
| Buffer | Experimental conditions | Acid peak % | Main Peak % | Alkaline Peak % | SEC-HPLC Main peak |
| Citric acid | 37 □ for 7 days | 35.90 | 55.60 | 8.50 | 94.43 |
| Citric acid + 2% Sorbitol | 37 □ for 7 days | 35.85 | 55.88 | 8.27 | 94.10 |
| Citric acid + 1.5% Trehalose | 37 □ for 7 days | 36.30 | 55.20 | 8.50 | 93.46 |
| Histidine | 37 □ for 7 days | 34.60 | 57.50 | 7.90 | 96.57 |
| Histidine + 2% Sorbitol | 37 □ for 7 days | 34.60 | 57.60 | 7.70 | 96.21 |
| Histidine + 1.5% Trehalose | 37 □ for 7 days | 34.38 | 57.92 | 7.70 | 94.40 |

After sodium chloride was added to the histidine buffer system, the opalescence of the humanized antibody hu1044 increased significantly. The higher the salt concentration, the more obvious the opalescence, thus indicating that when the humanized antibody was in the histidine buffer system, it was more stable without salt or with low salt.

The humanized antibody hu1044 in histidine buffer was subjected to a two-week accelerated stability test at 37□, detecting the quality changes of IEX-HPLC, SEC-HPLC and non-reduced CE-SDS. The results showed that as time increased, the purity of SEC-HPLC slowly decreased, but at day 14, the purity of SEC was still above 98%, and the acid peak of IEX-HPLC slightly increased, and the alkaline peak basically unchanged, and non-reduced CE-SDS was slightly reduced, see Table 6.

TABLE 6

Humanrized antibody hu1044 preparation buffer Screen III

| Experimental conditions | IEX-HPLC | | | SEC-HPLC Main peak | Non-reduced CE-SDS main peak |
| --- | --- | --- | --- | --- | --- |
| | Acid peak % | Main Peak % | Alkaline Peak % | | |
| 37 □ for 0 day | 24.87 | 61.93 | 13.21 | 99.34 | 97.16 |
| 37 □ for 4 days | 25.11 | 62.96 | 11.93 | 99.02 | / |
| 37 □ for 6 days | / | / | / | / | 97.1 |
| 37 □ for 8 days | 26.35 | 60.34 | 13.3 | 98.91 | / |
| 37 □ for 12 days | 27.7 | 59.12 | 13.18 | 98.75 | / |
| 37 □ for 14 days | 27.92 | 59.15 | 12.93 | 98.70 | 96.6 |

The humanized antibody hu1044 exhibited different stabilities in different buffers, wherein the charge heterogeneity of the antibody easily changed in the phosphate buffer system, while it was relatively stable in citrate buffer and histidine buffer. The increase of salt ions obviously led to the increase of opalescence of humanized antibody, confirming that the antibody was not suitable for higher salt buffer. Excipients such as trehalose and sorbitol had no significant effect on the stability of the antibody. The above screening results confirmed that the humanized antibody had the highest stability in 2 mM histidine buffer (containing 0.07% Tween-80, pH6.0).

All publications mentioned herein are incorporated by reference as if each individual document was cited as a reference in the present application. It should be understood that, after reading the above teachings of the present invention, those skilled in the art can make various modifications and changes. These equivalent forms are also within the scope defined by the claims appended hereto.

The invention claimed is:

1. An anti-HER3 antibody, wherein the antibody comprises:
    a light chain variable region comprising an amino acid sequence selected from the group consisting of: SEQ ID NO: 3 and SEQ ID NO: 7 and a heavy chain variable region comprising an amino acid sequence selected from the group consisting of: SEQ ID NO: 4 and SEQ ID NO: 8.

2. The antibody of claim 1, wherein the antibody is a humanized antibody.

3. The antibody of claim 1, wherein the antibody is a double-chain antibody or a single-chain antibody.

4. The antibody of claim 1, wherein the antibody comprises:
    a light chain variable region comprising SEQ ID NO: 7 and a heavy chain variable region comprising SEQ ID NO: 8; or
    a light chain variable region comprising SEQ ID NO: 3 and a heavy chain variable region comprising SEQ ID NO: 4.

5. A recombinant protein, wherein the recombinant protein comprises:
    (i) the antibody of claim 1; and
    (ii) an optional tag sequence to assist expression and/or purification.

6. An antibody preparation, wherein the antibody preparation comprises:
    (a) the antibody of claim 1; and
    (b) a carrier, which includes buffers, sterile water, and optional surfactants.

7. A kit, wherein the kit comprises the antibody preparation of claim 6 and a container for containing the antibody preparation.

8. A CAR construct, wherein the scFv segment of the antigen binding domain of the CAR construct is the binding region specifically binding HER3, and the ScFv comprises the light chain variable region and the heavy chain variable region of the antibody of claim 1.

9. An antibody-drug conjugate, wherein the antibody-drug conjugate comprises:
    (a) an antibody moiety, which is selected from the group consisting of: the antibody of claim 1; and
    (b) a coupling moiety coupled to the antibody moiety, which is selected from the group consisting of: a detectable label, a drug, a toxin, a cytokine, a radionuclide, an enzyme, and a combination thereof.

10. The antibody preparation of claim 6, wherein the concentration of the antibody in the preparation is 5-100 mg/mL.

11. The antibody preparation of claim 6, wherein the buffer is selected from the group consisting of: a citric acid buffer system, a histidine buffer system, and a combination thereof.

12. The antibody preparation of claim 11, wherein the buffer is a histidine buffer system, and the concentration of the histidine buffer system in the preparation is 0.5-20 mM.

13. The antibody preparation of claim 6, wherein the surfactant is selected from the group consisting of: polysorbate 80, polysorbate 20, and a combination thereof.

14. The antibody preparation of claim 6, wherein the pH of the preparation ranges from 5.0 to 7.5.

15. A method for treating HER3-related diseases, wherein the method comprises: administering the antibody of claim 1, an antibody-drug conjugate of the antibody, a CAR-T cell expressing the antibody, or a combination thereof to a subject in need thereof.

* * * * *

SEQUENCE LISTING

<160> NUMBER OF SEQ ID NOS: 10

<210> SEQ ID NO 1
<211> LENGTH: 113
<212> TYPE: PRT
<213> ORGANISM: artificial sequence
<220> FEATURE:
<223> OTHER INFORMATION: h1044-0 VL

<400> SEQUENCE: 1

Asp Ile Val Met Thr Gln Ser Pro Gly Thr Leu Ser Leu Ser Pro Gly
1               5                   10                  15

Glu Arg Ala Thr Leu Ser Cys Arg Ser Ser Lys Ser Leu Leu His Ser
            20                  25                  30

Asn Gly Ile Thr Tyr Leu Tyr Trp Tyr Gln Gln Lys Pro Gly Gln Ala

```
                35                  40                  45
Pro Arg Leu Leu Ile Tyr Gln Met Ser Asn Leu Ala Ser Gly Ile Pro
        50                  55                  60

Asp Arg Phe Ser Gly Ser Gly Ser Gly Thr Asp Phe Thr Leu Thr Ile
 65                  70                  75                  80

Ser Arg Leu Glu Pro Glu Asp Phe Ala Val Tyr Tyr Cys Ala Gln Asn
                85                  90                  95

Leu Glu Leu Pro Trp Thr Phe Gly Gln Gly Thr Lys Val Glu Ile Lys
            100                 105                 110

Arg

<210> SEQ ID NO 2
<211> LENGTH: 117
<212> TYPE: PRT
<213> ORGANISM: artificial sequence
<220> FEATURE:
<223> OTHER INFORMATION: h1044-0 VH

<400> SEQUENCE: 2

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Asn Tyr
                20                  25                  30

Trp Ile Asp Trp Val Arg Gln Ala Pro Gly Gln Gly Leu Glu Trp Met
            35                  40                  45

Gly Glu Ile Leu Pro Gly Ser Gly Gly Thr Asp Tyr Asn Glu Lys Phe
        50                  55                  60

Lys Gly Arg Val Thr Ile Thr Ala Asp Thr Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Asp Asp Tyr Asp Val Phe Ala Tyr Trp Gly Gln Gly Thr Leu
            100                 105                 110

Val Thr Val Ser Ser
        115

<210> SEQ ID NO 3
<211> LENGTH: 113
<212> TYPE: PRT
<213> ORGANISM: artificial sequence
<220> FEATURE:
<223> OTHER INFORMATION: hu1044 VL

<400> SEQUENCE: 3

Asp Ile Val Met Thr Gln Ser Pro Gly Thr Leu Ser Leu Ser Pro Gly
 1               5                  10                  15

Glu Arg Ala Thr Leu Ser Cys Arg Ser Ser Lys Ser Leu Leu His Ser
                20                  25                  30

Asn Gly Ile Thr Tyr Leu Tyr Trp Tyr Gln Gln Lys Pro Gly Gln Ala
            35                  40                  45

Pro Arg Leu Leu Ile Tyr Gln Met Ser Asn Leu Ala Ser Gly Ile Pro
        50                  55                  60

Asp Arg Phe Ser Ser Gly Ser Gly Thr Asp Phe Thr Leu Thr Ile
 65                  70                  75                  80

Ser Arg Leu Glu Pro Glu Asp Phe Ala Val Tyr Tyr Cys Ala Gln Asn
                85                  90                  95

Leu Glu Leu Pro Trp Thr Phe Gly Gln Gly Thr Lys Val Glu Ile Lys
```

-continued

```
                100                 105                 110
Arg

<210> SEQ ID NO 4
<211> LENGTH: 117
<212> TYPE: PRT
<213> ORGANISM: artificial sequence
<220> FEATURE:
<223> OTHER INFORMATION: hu1044 VH

<400> SEQUENCE: 4

Gln Val Gln Leu Val Gln Ser Gly Ala Glu Val Lys Lys Pro Gly Ser
1               5                  10                 15

Ser Val Lys Val Ser Cys Lys Ala Ser Gly Gly Thr Phe Ser Asn Tyr
            20                  25                  30

Trp Ile Asp Trp Val Lys Gln Ala Pro Gly Gln Gly Leu Glu Trp Met
        35                  40                  45

Gly Glu Ile Leu Pro Gly Ser Gly Gly Thr Asp Tyr Asn Glu Lys Phe
    50                  55                  60

Lys Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Tyr Asp Val Phe Ala Tyr Trp Gly Gln Gly Thr Leu
            100                 105                 110

Val Thr Val Ser Ser
        115

<210> SEQ ID NO 5
<211> LENGTH: 113
<212> TYPE: PRT
<213> ORGANISM: Mus musculus

<400> SEQUENCE: 5

Asp Ile Val Met Thr Gln Ala Ala Phe Ser Asn Pro Val Thr Leu Gly
1               5                  10                 15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Leu Glu Ile Lys
            100                 105                 110

Arg

<210> SEQ ID NO 6
<211> LENGTH: 117
<212> TYPE: PRT
<213> ORGANISM: Mus musculus

<400> SEQUENCE: 6

Glu Val Gln Leu Gln Gln Ser Gly Thr Glu Leu Met Lys Pro Gly Ala
1               5                  10                 15
```

Ser Val Lys Ile Ser Cys Lys Ala Thr Gly Gly Thr Phe Ser Asn Tyr
            20                  25                  30

Trp Ile Asp Trp Val Lys Gln Arg Pro Gly His Gly Leu Glu Trp Ile
        35                  40                  45

Gly Glu Ile Leu Pro Gly Ser Gly Gly Thr Asp Tyr Asn Glu Lys Phe
50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Asp Tyr Asp Val Phe Ala Tyr Trp Gly Gln Gly Thr Leu
            100                 105                 110

Val Thr Val Ser Ala
        115

<210> SEQ ID NO 7
<211> LENGTH: 113
<212> TYPE: PRT
<213> ORGANISM: artificial sequence
<220> FEATURE:
<223> OTHER INFORMATION: hu1044-7 VL

<400> SEQUENCE: 7

Asp Ile Val Met Thr Gln Ser Pro Gly Thr Leu Ser Leu Ser Pro Gly
1               5                   10                  15

Glu Arg Ala Thr Leu Ser Cys Arg Ser Ser Lys Ser Leu Leu His Ser
            20                  25                  30

Asn Gly Ile Thr Tyr Leu Tyr Trp Tyr Gln Gln Lys Pro Gly Gln Ala
        35                  40                  45

Pro Arg Leu Leu Ile Tyr Gln Met Ser Asn Leu Ala Ser Gly Val Pro
50                  55                  60

Asp Arg Phe Ser Ser Ser Gly Ser Gly Thr Asp Phe Thr Leu Thr Ile
65                  70                  75                  80

Ser Arg Leu Glu Pro Glu Asp Phe Ala Val Tyr Tyr Cys Ala Gln Asn
                85                  90                  95

Leu Glu Leu Pro Trp Thr Phe Gly Gln Gly Thr Lys Val Glu Ile Lys
            100                 105                 110

Arg

<210> SEQ ID NO 8
<211> LENGTH: 117
<212> TYPE: PRT
<213> ORGANISM: artificial sequence
<220> FEATURE:
<223> OTHER INFORMATION: hu1044-7 VH

<400> SEQUENCE: 8

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Trp Ile Asp Trp Val Arg Gln Ala Pro Gly Gln Gly Leu Glu Trp Met
        35                  40                  45

Gly Glu Ile Leu Pro Gly Ser Gly Gly Thr Asp Tyr Asn Glu Lys Phe
50                  55                  60

Lys Gly Lys Ala Thr Ile Thr Ala Asp Thr Ser Thr Ser Thr Ala Tyr
65                  70                  75                  80

```
Met Glu Leu Ser Ser Leu Arg Ser Glu Asp Thr Ala Val Tyr Tyr Cys
                85                  90                  95

Ala Arg Asp Asp Tyr Asp Val Phe Ala Tyr Trp Gly Gln Gly Thr Leu
            100                 105                 110

Val Thr Val Ser Ser
        115

<210> SEQ ID NO 9
<211> LENGTH: 113
<212> TYPE: PRT
<213> ORGANISM: artificial sequence
<220> FEATURE:
<223> OTHER INFORMATION: h_VL

<400> SEQUENCE: 9

Glu Ile Val Leu Thr Gln Ser Pro Gly Thr Leu Ser Leu Ser Pro Gly
1               5                   10                  15

Glu Arg Ala Thr Leu Ser Cys Arg Ser Ser Lys Ser Leu Leu His Ser
            20                  25                  30

Asn Gly Ile Thr Tyr Leu Tyr Trp Tyr Gln Gln Lys Pro Gly Gln Ala
        35                  40                  45

Pro Arg Leu Leu Ile Tyr Gln Met Ser Asn Leu Ala Ser Gly Ile Pro
    50                  55                  60

Asp Arg Phe Ser Gly Ser Gly Ser Gly Thr Asp Phe Thr Leu Thr Ile
65                  70                  75                  80

Ser Arg Leu Glu Pro Glu Asp Phe Ala Val Tyr Tyr Cys Ala Gln Asn
                85                  90                  95

Leu Glu Leu Pro Trp Thr Phe Gly Gln Gly Thr Lys Val Glu Ile Lys
            100                 105                 110

Arg

<210> SEQ ID NO 10
<211> LENGTH: 117
<212> TYPE: PRT
<213> ORGANISM: artificial sequence
<220> FEATURE:
<223> OTHER INFORMATION: h_VH

<400> SEQUENCE: 10

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Trp Ile Asp Trp Val Arg Gln Ala Pro Gly Gln Gly Leu Glu Trp Met
        35                  40                  45

Gly Glu Ile Leu Pro Gly Ser Gly Gly Thr Asp Tyr Asn Glu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Tyr Asp Val Phe Ala Tyr Trp Gly Gln Gly Thr Leu
            100                 105                 110

Val Thr Val Ser Ser
        115
```